US010519223B2

(12) United States Patent
Mercken et al.

(10) Patent No.: US 10,519,223 B2
(45) Date of Patent: Dec. 31, 2019

(54) ANTIBODIES TO PYROGLUTAMATE AMYLOID-β AND USES THEREOF

(71) Applicant: JANSSEN PHARMACEUTICA NV, Beerse (BE)

(72) Inventors: Marc Mercken, Turnhout (BE); Bianca Van Broeck, Schilde (BE); Marc Vandermeeren, Geel (BE); Bart Hermans, Beerse (BE); Astrid Bottelbergs, Antwerp (BE)

(73) Assignee: Jannsen Pharmaceutica NV, Beerse (BE)

(*) Notice: Subject to any disclaimer, the term of this patent is extended or adjusted under 35 U.S.C. 154(b) by 0 days.

(21) Appl. No.: 15/801,435

(22) Filed: Nov. 2, 2017

(65) Prior Publication Data
US 2018/0142011 A1 May 24, 2018

Related U.S. Application Data

(60) Provisional application No. 62/416,788, filed on Nov. 3, 2016.

(51) Int. Cl.
A61K 39/395 (2006.01)
A61K 39/00 (2006.01)
C12P 21/08 (2006.01)
C07K 16/00 (2006.01)
G01N 33/53 (2006.01)
A61K 49/00 (2006.01)
A61K 49/16 (2006.01)
C07K 16/18 (2006.01)
G01N 33/68 (2006.01)
A61P 25/28 (2006.01)
G01N 33/533 (2006.01)
C12Q 1/37 (2006.01)

(52) U.S. Cl.
CPC .......... C07K 16/18 (2013.01); A61K 39/3955 (2013.01); A61P 25/28 (2018.01); G01N 33/6896 (2013.01); A01K 2267/0312 (2013.01); A61K 2039/505 (2013.01); C07K 2317/24 (2013.01); C07K 2317/33 (2013.01); C07K 2317/34 (2013.01); C07K 2317/51 (2013.01); C07K 2317/515 (2013.01); C07K 2317/56 (2013.01); C07K 2317/565 (2013.01); C07K 2317/567 (2013.01); C07K 2317/92 (2013.01); C12Q 1/37 (2013.01); G01N 33/533 (2013.01); G01N 2333/4709 (2013.01); G01N 2333/96425 (2013.01); G01N 2800/2814 (2013.01); G01N 2800/2821 (2013.01)

(58) Field of Classification Search
CPC .............. C07K 16/18; C07K 2317/24; C07K 2317/33; C07K 2317/56; C07K 2317/565; C07K 2317/92; C07K 2317/34; C07K 2317/55; C07K 2317/567; C07K 2317/94; C07K 2317/51; C07K 2317/515; C07K 2317/76; C07K 14/4711; A61K 2039/505; A61K 39/3955; A61K 31/4439; A61K 39/395; A61K 49/00; G01N 2333/96425; G01N 33/533; G01N 2333/4709; G01N 33/6896; G01N 2800/2814; G01N 2800/2821; A61P 25/28; A01K 2267/0312; C12Q 1/37
See application file for complete search history.

(56) References Cited

U.S. PATENT DOCUMENTS

| | | | |
|---|---|---|---|
| 4,166,452 A | 9/1979 | Generales, Jr. | |
| 5,587,458 A | 12/1996 | King et al. | |
| 5,642,870 A | 7/1997 | Sargis | |
| 5,761,894 A | 6/1998 | Evans | |
| 8,058,405 B2 * | 11/2011 | Demuth | C07K 16/18 530/388.1 |
| 8,679,498 B2 * | 3/2014 | Lu | C07K 16/18 424/142.1 |
| 8,858,949 B2 * | 10/2014 | Yokoseki | C07K 16/18 424/172.1 |
| 8,961,972 B2 * | 2/2015 | Lu | C07K 16/18 424/142.1 |
| 9,585,956 B2 | 3/2017 | Pfeifer | |
| 9,828,420 B2 | 11/2017 | Nitsch | |
| 9,863,961 B2 | 1/2018 | Sarasa Barrio | |
| 9,907,485 B2 | 3/2018 | Hartlep | |
| 9,944,696 B2 | 4/2018 | Demattos | |
| 2015/0094218 A1 | 4/2015 | Piazza | |
| 2017/0204171 A1 | 7/2017 | DeMattos et al. | |
| 2017/0363645 A1 | 12/2017 | Kleinschmidt | |
| 2018/0140689 A1 | 5/2018 | Kleinschmidt | |
| 2018/0305444 A1 | 10/2018 | Demattos | |
| 2019/0046536 A1 | 2/2019 | Demattos | |

FOREIGN PATENT DOCUMENTS

| | | | | |
|---|---|---|---|---|
| WO | WO2007062852 | * | 6/2007 | ............ C07K 16/18 |
| WO | 2010004434 A2 | | 1/2010 | |
| WO | 2010009987 | | 1/2010 | |
| WO | 2011151076 | | 12/2011 | |
| WO | 2012021469 | | 2/2012 | |
| WO | WO2012021475 | * | 2/2012 | ........... A61K 39/395 |
| WO | 2015191825 | | 12/2015 | |
| WO | 2016097305 | | 6/2016 | |
| WO | 2017009459 | | 1/2017 | |
| WO | 2017/202779 A1 | | 11/2017 | |
| WO | 2017/211827 | | 12/2017 | |
| WO | 2018/031361 A2 | | 2/2018 | |
| WO | 2018/75339 A1 | | 4/2018 | |
| WO | 2019/040612 A1 | | 2/2019 | |

OTHER PUBLICATIONS

Burgess et al. J of Cell Bio. 1990, 111:2129-2138.*

(Continued)

Primary Examiner — Chang-Yu Wang

(57) ABSTRACT

The invention provides an antibody or antigen binding fragments thereof that binds to 3pE Aβ and methods of making and using the antibody or antigen binding fragment thereof, including use for formulations, administration and kits. The antibody and antigen binding fragments thereof and methods disclosed are useful for diagnosis, prognosis and treatment of Alzheimer's disease or other β-amyloid-related diseases.

16 Claims, 11 Drawing Sheets

Specification includes a Sequence Listing.

(56) References Cited

OTHER PUBLICATIONS

Pawson et al. 2003, Science 300:445-452.*
Alaoui-Ismaili et al., Cytokine Growth Factor Rev. 2009; 20:501-507.*
Guo et al., PNAS 2004; 101:9205-9210.*
Rudikoff et al. Proc. Natl. Acad. Sci. USA 1982 vol. 79: p. 1979.*
Pandey Intl. J. Pharma. Sci. Rev. Res 2010; 1: 88-94.*
Laffleur et al. Chapter 9, Antibody Methods and Protocols, Methods in Molecular Biology, edited by Gabriele Proetzel and Hilmar Ebersbach, 2012; vol. 901: 149-159; DOI 10.1007/978-1-61779-931-0_9.*
Glukhova et al. Curr. Pharma. Design, 2016; 22:870-878.*
Zhang, Chapter 7, Antibody Methods and Protocols, Methods in Molecular Biology, edited by Gabriele Proetzel and Hilmar Ebersbach, 2012; vol. 901: 117-159; DOI 10.1007/978-1-61779-931-0_7.*
Lee et al., Chapter 8, Antibody Methods and Protocols, Methods in Molecular Biology, edited by Gabriele Proetzel and Hilmar Ebersbach, 2012; vol. 901: 137-148; DOI 10.1007/978-1-61779-931-0_8.*
Carter, et al., High Level *Escherichia coli* Expression and Production of a Bivalent Humanized Antibody Fragment, Bio/technology, 1992, pp. 163-167, vol. 10.
Chothia, et al., Conformations of immunoglobulin hypervariable regions, Nature, 1989, pp. 877-883, vol. 342.
Cynis, et al., Immunotherapy targeting pyroglutamate-3 Aβ: prospects and challenges, Molecular Neurodegeneration, 2016, pp. 1-11, vol. 11 issue 48.
Cynthia A Lemere., Immunotherapy for Alzheimer's disease: hoops and hurdles, Lemere Molecular Neurodegeneration, 2013, pp. 1-6, vol. 8 Issue 36.
De Kimpe, et al., Intracellular accumulation of aggregated pyroglutamate amyloid beta: convergence of aging and Aβ pathology at the lysosome, Age, 2013, pp. 673-687, vol. 35.
Demattos, et al., A Plaque-Specific Antibody Clears Existing b-amyloid Plaques in Alzheimer's Disease Mice, Neuron, Dec. 6, 2012, pp. 908-920, vol. 76.
Frost, et al., An anti-pyroglutamate-3 Aβ vaccine reduces plaques and improves cognition in APPswe/PS1ΔE9 mice, Neurobiol Aging, 2015, pp. 3187-3199, vol. 36 Issue 12.
Frost, et al., Passive Immunization against Pyroglutamate-3 Amyloid—Reduces Plaque Burden in Alzheimer-Like Transgenic Mice: A Pilot Study, Neurodegenerative Diseases, Feb. 16, 2012, pp. 265-270, vol. 10.
Frost, et al., Pyroglutamate-3 Amyloid-b Deposition in the Brains of Humans, Non-Human Primates, Canines, and Alzheimer Disease Like Transgenic Mouse Models, The American Journal of Pathology, 2013, pp. 369-381, vol. 183 Issue 2.
Huse, et al., Generation of a Large Combinatorial Library of the Immunoglobulin Repertoire in Phage Lambda, Research Article, 1989, pp. 1275-1281, vol. 246.
Jawhar, et al., Pyroglutamate Amyloid-(A): A Hatchet Man in Alzheimer Disease*, The Journal of Biological Chemistry, Nov. 11, 2011, pp. 38625-36832, vol. 286 Issue 45.
Kohler, et al., Continuous cultures of fused cells secreting antibody of predefined specificity, Nature, Aug. 7, 1975, pp. 495-497, vol. 256.
Kohler, et al., Fusion between immunoglobulin-secreting and nonsecreting myeloma cell lines, Eur. J. Immunol, 1976, pp. 292-295, vol. 6.
Lefranc, et al., IMGT R , the international ImMunoGeneTics information system R 25 years on, Nucleic Acids Research, Nov. 5, 2014, pp. D413-D422, vol. 43.
Lefranc, et al., IMGT, the international ImMunoGeneTics database, Nucleic Acids Research, 1999, pp. 209-212, vol. 21 Issue 1.
Lefranc, et al., Nomenclature of the Human Immunoglobulin Heavy (IGH) Genes, Experimental and Clinical Immunogenetics, 2001, pp. 100-116, vol. 18.
Lefranc, et al., Nomenclature of the Human Immunoglobulin Kappa (IGK) Genes, Experimental and Clinical Immunogenetics, 2001, pp. 161-174, vol. 18.
Lefranc, et al., Nomenclature of the Human Immunoglobulin Lambda (IGL) Genes, Experimental and Clinical Immunogenetics, 2001, pp. 242-254, vol. 18.
Liu, et al., N-terminal Glutamate to Pyroglutamate Conversion in Vivo for Human IgG2 Antibodies, The Journal of Biological Chemistry, Apr. 1, 2011, pp. 11211-11217, vol. 286 Issue 13.
Scaviner, et al., Protein Displays of the Human Immunoglobulin Heavy, Kappa and Lambda Variable and Joining Regions, Experimental and Clinical Immunogenetics, 1999, pp. 234-240, vol. 16.
Venkataramani, et al., Antibody 9D5 Recognizes Oligomeric Pyroglutamate Amyloid—in a Fraction of Amyloid-Deposits in Alzheimer's Disease without Cross-Reactivity with other Protein Aggregates, Journal of Alzheimer's Disease, 2012, pp. 361-371, vol. 29.
ISR PCT/IB2017/056832, dated Feb. 2, 2018.

* cited by examiner

```
                    1 3                                              42
      Aβ1-42        DAEFRHDSGYEVHHQKLVFFAEDVGSNKGAIIGLMVGGVVIA

Aβ3E-42         EFRHDSGYEVHHQKLVFFAEDVGSNKGAIIGLMVGGVVIA

Aβ3(pE)-42     pEFRHDSGYEVHHQKLVFFAEDVGSNKGAIIGLMVGGVVIA
```

FIG. 1

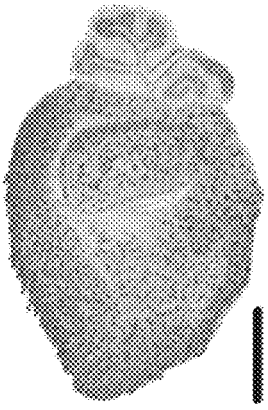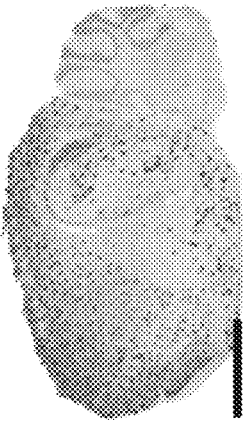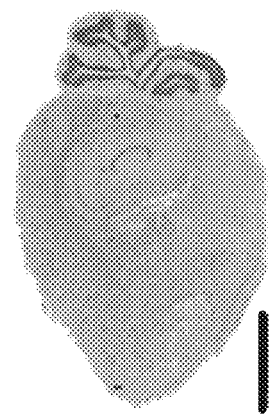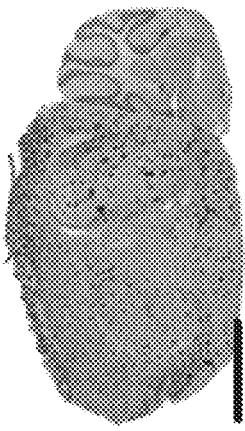

SEQUENCE LISTING

<160> NUMBER OF SEQ ID NOS: 31

<210> SEQ ID NO 1
<211> LENGTH: 449
<212> TYPE: PRT
<213> ORGANISM: Mus musculus
<220> FEATURE:
<221> NAME/KEY: CHAIN
<222> LOCATION: (1)..(449)
<223> OTHER INFORMATION: Heavy Chain

<400> SEQUENCE: 1

Gln Val Gln Leu Gln Gln Pro Gly Ala Glu Leu Val Arg Pro Gly Ala
1               5                   10                  15

Ser Val Lys Leu Ser Cys Lys Thr Ser Gly Tyr Thr Phe Thr Arg Tyr
            20                  25                  30

Trp Ile Asn Trp Val Lys Gln Arg Pro Gly Gln Gly Leu Glu Trp Ile
        35                  40                  45

Gly Asn Ile Arg Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Asn Arg Pro Thr Ser Glu Asp Ser Ala Val Tyr Tyr Cys
                85                  90                  95

Thr Arg Glu Gly Ala Tyr Ser Asp Tyr Glu Thr Tyr Trp Gly Gln Gly
            100                 105                 110

Thr Leu Val Thr Val Ser Ala Ala Lys Thr Thr Ala Pro Ser Val Tyr
        115                 120                 125

Pro Leu Ala Pro Val Cys Gly Asp Thr Thr Gly Ser Ser Val Thr Leu
    130                 135                 140

Gly Cys Leu Val Lys Gly Tyr Phe Pro Glu Pro Val Thr Leu Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Thr Ser Ser
            180                 185                 190

Thr Trp Pro Ser Gln Ser Ile Thr Cys Asn Val Ala His Pro Ala Ser
        195                 200                 205

Ser Thr Lys Val Asp Lys Lys Ile Glu Pro Arg Gly Pro Thr Ile Lys
    210                 215                 220

Pro Cys Pro Pro Cys Lys Cys Pro Ala Pro Asn Leu Leu Gly Gly Pro
225                 230                 235                 240

Ser Val Phe Ile Phe Pro Pro Lys Ile Lys Asp Val Leu Met Ile Ser
                245                 250                 255

Leu Ser Pro Ile Val Thr Cys Val Val Val Asp Val Ser Glu Asp Asp
            260                 265                 270

Pro Asp Val Gln Ile Ser Trp Phe Val Asn Asn Val Glu Val His Thr
        275                 280                 285

Ala Gln Thr Gln Thr His Arg Glu Asp Tyr Asn Ser Thr Leu Arg Val
    290                 295                 300

Val Ser Ala Leu Pro Ile Gln His Gln Asp Trp Met Ser Gly Lys Glu
305                 310                 315                 320

Phe Lys Cys Lys Val Asn Asn Lys Asp Leu Pro Ala Pro Ile Glu Arg
                325                 330                 335

Thr Ile Ser Lys Pro Lys Gly Ser Val Arg Ala Pro Gln Val Tyr Val
            340                 345                 350

-continued

Leu Pro Pro Pro Glu Glu Met Thr Lys Lys Gln Val Thr Leu Thr
            355                 360                 365

Cys Met Val Thr Asp Phe Met Pro Glu Asp Ile Tyr Val Glu Trp Thr
370                 375                 380

Asn Asn Gly Lys Thr Glu Leu Asn Tyr Lys Asn Thr Glu Pro Val Leu
385                 390                 395                 400

Asp Ser Asp Gly Ser Tyr Phe Met Tyr Ser Lys Leu Arg Val Glu Lys
                405                 410                 415

Lys Asn Trp Val Glu Arg Asn Ser Tyr Ser Cys Ser Val Val His Glu
                420                 425                 430

Gly Leu His Asn His Thr Thr Lys Ser Phe Ser Arg Thr Pro Gly
            435                 440                 445

Lys

<210> SEQ ID NO 2
<211> LENGTH: 119
<212> TYPE: PRT
<213> ORGANISM: Mus musculus
<220> FEATURE:
<221> NAME/KEY: DOMAIN
<222> LOCATION: (1)..(119)
<223> OTHER INFORMATION: VH

<400> SEQUENCE: 2

Gln Val Gln Leu Gln Gln Pro Gly Ala Glu Leu Val Arg Pro Gly Ala
1               5                   10                  15

Ser Val Lys Leu Ser Cys Lys Thr Ser Gly Tyr Thr Phe Thr Arg Tyr
            20                  25                  30

Trp Ile Asn Trp Val Lys Gln Arg Pro Gly Gln Gly Leu Glu Trp Ile
        35                  40                  45

Gly Asn Ile Arg Pro Ser Asp Ser Tyr Thr Asn Tyr Asn Gln Lys Phe
    50                  55                  60

Lys Asp Lys Ala Thr Leu Thr Val Asp Lys Ser Ser Ser Thr Ala Tyr
65                  70                  75                  80

Met Gln Leu Asn Arg Pro Thr Ser Glu Asp Ser Ala Val Tyr Tyr Cys
                85                  90                  95

Thr Arg Glu Gly Ala Tyr Ser Asp Tyr Glu Thr Tyr Trp Gly Gln Gly
            100                 105                 110

Thr Leu Val Thr Val Ser Ala
        115

<210> SEQ ID NO 3
<211> LENGTH: 5
<212> TYPE: PRT
<213> ORGANISM: Mus musculus
<220> FEATURE:
<221> NAME/KEY: DOMAIN
<222> LOCATION: (1)..(5)
<223> OTHER INFORMATION: HCDR1 (Kabat)

<400> SEQUENCE: 3

Arg Tyr Trp Ile Asn
1               5

<210> SEQ ID NO 4
<211> LENGTH: 17
<212> TYPE: PRT
<213> ORGANISM: Mus musculus

```
<220> FEATURE:
<221> NAME/KEY: DOMAIN
<222> LOCATION: (1)..(17)
<223> OTHER INFORMATION: HCDR2 (Kabat)

<400> SEQUENCE: 4

Asn Ile Arg Pro Ser Asp Ser Tyr Thr Asn Tyr Asn Gln Lys Phe Lys
1               5                   10                  15
Asp

<210> SEQ ID NO 5
<211> LENGTH: 10
<212> TYPE: PRT
<213> ORGANISM: Mus musculus
<220> FEATURE:
<221> NAME/KEY: DOMAIN
<222> LOCATION: (1)..(10)
<223> OTHER INFORMATION: HCDR3 (Kabat)

<400> SEQUENCE: 5

Glu Gly Ala Tyr Ser Asp Tyr Glu Thr Tyr
1               5                   10

<210> SEQ ID NO 6
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: HCDR1 (Chothia)

<400> SEQUENCE: 6

Gly Tyr Thr Phe Thr Arg Tyr
1               5

<210> SEQ ID NO 7
<211> LENGTH: 6
<212> TYPE: PRT
<213> ORGANISM: Mus musculus
<220> FEATURE:
<221> NAME/KEY: DOMAIN
<222> LOCATION: (1)..(6)
<223> OTHER INFORMATION: HCDR2 (Chothia)

<400> SEQUENCE: 7

Arg Pro Ser Asp Ser Tyr
1               5

<210> SEQ ID NO 8
<211> LENGTH: 9
<212> TYPE: PRT
<213> ORGANISM: Mus musculus
<220> FEATURE:
<221> NAME/KEY: DOMAIN
<222> LOCATION: (1)..(9)
<223> OTHER INFORMATION: HCDR3 (Chothia)

<400> SEQUENCE: 8

Glu Gly Ala Tyr Ser Asp Tyr Glu Thr
1               5

<210> SEQ ID NO 9
<211> LENGTH: 8
<212> TYPE: PRT
<213> ORGANISM: Mus musculus
```

```
<220> FEATURE:
<221> NAME/KEY: DOMAIN
<222> LOCATION: (1)..(8)
<223> OTHER INFORMATION: HCDR1 (IMGT)

<400> SEQUENCE: 9

Gly Tyr Thr Phe Thr Arg Tyr Trp
1               5

<210> SEQ ID NO 10
<211> LENGTH: 8
<212> TYPE: PRT
<213> ORGANISM: Mus musculus
<220> FEATURE:
<221> NAME/KEY: DOMAIN
<222> LOCATION: (1)..(8)
<223> OTHER INFORMATION: HCDR2 (IMGT)

<400> SEQUENCE: 10

Ile Arg Pro Ser Asp Ser Tyr Thr
1               5

<210> SEQ ID NO 11
<211> LENGTH: 12
<212> TYPE: PRT
<213> ORGANISM: Mus musculus
<220> FEATURE:
<221> NAME/KEY: DOMAIN
<222> LOCATION: (1)..(12)
<223> OTHER INFORMATION: HCDR3 (IMGT)

<400> SEQUENCE: 11

Thr Arg Glu Gly Ala Tyr Ser Asp Tyr Glu Thr Tyr
1               5                   10

<210> SEQ ID NO 12
<211> LENGTH: 219
<212> TYPE: PRT
<213> ORGANISM: Mus musculus
<220> FEATURE:
<221> NAME/KEY: CHAIN
<222> LOCATION: (1)..(219)
<223> OTHER INFORMATION: Light Chain

<400> SEQUENCE: 12

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
                20                  25                  30

Asn Gly Lys Thr Tyr Leu Asn Trp Leu Leu Gln Arg Pro Gly Gln Ser
            35                  40                  45

Pro Lys Arg Leu Ile Tyr Leu Val Ser Lys Leu Asp Ser Gly Val Pro
        50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Gly Gly Thr Lys Leu Glu Ile Lys
            100                 105                 110

Arg Ala Asp Ala Ala Pro Thr Val Ser Ile Phe Pro Pro Ser Ser Glu
        115                 120                 125

Gln Leu Thr Ser Gly Gly Ala Ser Val Val Cys Phe Leu Asn Asn Phe
    130                 135                 140
```

Tyr Pro Lys Asp Ile Asn Val Lys Trp Lys Ile Asp Gly Ser Glu Arg
145                 150                 155                 160

Gln Asn Gly Val Leu Asn Ser Trp Thr Asp Gln Asp Ser Lys Asp Ser
                165                 170                 175

Thr Tyr Ser Met Ser Ser Thr Leu Thr Leu Thr Lys Asp Glu Tyr Glu
            180                 185                 190

Arg His Asn Ser Tyr Thr Cys Glu Ala Thr His Lys Thr Ser Thr Ser
        195                 200                 205

Pro Ile Val Lys Ser Phe Asn Arg Asn Glu Cys
    210                 215

<210> SEQ ID NO 13
<211> LENGTH: 112
<212> TYPE: PRT
<213> ORGANISM: Mus musculus
<220> FEATURE:
<221> NAME/KEY: DOMAIN
<222> LOCATION: (1)..(112)
<223> OTHER INFORMATION: VL

<400> SEQUENCE: 13

Asp Val Val Met Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Phe Thr Phe Gly Gly Gly Thr Lys Leu Glu Ile Lys
            100                 105                 110

<210> SEQ ID NO 14
<211> LENGTH: 16
<212> TYPE: PRT
<213> ORGANISM: Mus musculus
<220> FEATURE:
<221> NAME/KEY: DOMAIN
<222> LOCATION: (1)..(16)
<223> OTHER INFORMATION: LCDR1 (Kabat)

<400> SEQUENCE: 14

Lys Ser Ser Gln Ser Leu Leu Asp Ser Asn Gly Lys Thr Tyr Leu Asn
1               5                   10                  15

<210> SEQ ID NO 15
<211> LENGTH: 7
<212> TYPE: PRT
<213> ORGANISM: Mus musculus
<220> FEATURE:
<221> NAME/KEY: DOMAIN
<222> LOCATION: (1)..(7)
<223> OTHER INFORMATION: LCDR2 (Kabat)

<400> SEQUENCE: 15

Leu Val Ser Lys Leu Asp Ser
1               5

```
<210> SEQ ID NO 16
<211> LENGTH: 9
<212> TYPE: PRT
<213> ORGANISM: Mus musculus
<220> FEATURE:
<221> NAME/KEY: DOMAIN
<222> LOCATION: (1)..(9)
<223> OTHER INFORMATION: LCDR3 (Kabat) and LCDR3 (IMGT)

<400> SEQUENCE: 16

Val Gln Gly Thr His Phe Pro Phe Thr
 1               5

<210> SEQ ID NO 17
<211> LENGTH: 12
<212> TYPE: PRT
<213> ORGANISM: Mus musculus
<220> FEATURE:
<221> NAME/KEY: DOMAIN
<222> LOCATION: (1)..(12)
<223> OTHER INFORMATION: LCDR1 (Chothia)

<400> SEQUENCE: 17

Ser Gln Ser Leu Leu Asp Ser Asn Gly Lys Thr Tyr
 1               5                  10

<210> SEQ ID NO 18
<211> LENGTH: 3
<212> TYPE: PRT
<213> ORGANISM: Mus musculus
<220> FEATURE:
<221> NAME/KEY: DOMAIN
<222> LOCATION: (1)..(3)
<223> OTHER INFORMATION: LCDR2 (Chothia) and LCDR2 (IMGT)

<400> SEQUENCE: 18

Leu Val Ser
 1

<210> SEQ ID NO 19
<211> LENGTH: 6
<212> TYPE: PRT
<213> ORGANISM: Mus musculus
<220> FEATURE:
<221> NAME/KEY: DOMAIN
<222> LOCATION: (1)..(6)
<223> OTHER INFORMATION: LCDR3 (Chothia)

<400> SEQUENCE: 19

Gly Thr His Phe Pro Phe
 1               5

<210> SEQ ID NO 20
<211> LENGTH: 11
<212> TYPE: PRT
<213> ORGANISM: Mus musculus
<220> FEATURE:
<221> NAME/KEY: DOMAIN
<222> LOCATION: (1)..(11)
<223> OTHER INFORMATION: LCDR1 (IMGT)

<400> SEQUENCE: 20

Gln Ser Leu Leu Asp Ser Asn Gly Lys Thr Tyr
 1               5                  10
```

-continued

```
<210> SEQ ID NO 21
<211> LENGTH: 8
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is a pyroglutamate residue
<220> FEATURE:
<221> NAME/KEY: PEPTIDE
<222> LOCATION: (1)..(8)
<223> OTHER INFORMATION: peptide sequence from beta-amyloid

<400> SEQUENCE: 21

Xaa Phe Arg His Asp Ser Gly Cys
1               5

<210> SEQ ID NO 22
<211> LENGTH: 38
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is a pyroglutamate residue
<220> FEATURE:
<221> NAME/KEY: PEPTIDE
<222> LOCATION: (1)..(38)
<223> OTHER INFORMATION: peptide sequence from beta-amyloid

<400> SEQUENCE: 22

Xaa Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
        35

<210> SEQ ID NO 23
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: peptide sequence from beta-amyloid

<400> SEQUENCE: 23

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 24
<211> LENGTH: 38
<212> TYPE: PRT
<213> ORGANISM: Homo sapiens
<220> FEATURE:
<221> NAME/KEY: PEPTIDE
<222> LOCATION: (1)..(38)
<223> OTHER INFORMATION: peptide sequence from beta-amyloid
```

```
<400> SEQUENCE: 24

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val
            35

<210> SEQ ID NO 25
<211> LENGTH: 42
<212> TYPE: PRT
<213> ORGANISM: Homo sapiens
<220> FEATURE:
<221> NAME/KEY: PEPTIDE
<222> LOCATION: (1)..(42)
<223> OTHER INFORMATION: peptide sequence from beta-amyloid

<400> SEQUENCE: 25

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40

<210> SEQ ID NO 26
<211> LENGTH: 40
<212> TYPE: PRT
<213> ORGANISM: Homo sapiens
<220> FEATURE:
<221> NAME/KEY: PEPTIDE
<222> LOCATION: (1)..(40)
<223> OTHER INFORMATION: peptide sequence from beta-amyloid

<400> SEQUENCE: 26

Glu Phe Arg His Asp Ser Gly Tyr Glu Val His His Gln Lys Leu Val
1               5                   10                  15

Phe Phe Ala Glu Asp Val Gly Ser Asn Lys Gly Ala Ile Ile Gly Leu
            20                  25                  30

Met Val Gly Gly Val Val Ile Ala
            35                  40

<210> SEQ ID NO 27
<211> LENGTH: 30
<212> TYPE: PRT
<213> ORGANISM: Homo sapiens
<220> FEATURE:
<221> NAME/KEY: PEPTIDE
<222> LOCATION: (1)..(30)
<223> OTHER INFORMATION: peptide sequence from beta-amyloid

<400> SEQUENCE: 27

Glu Val His His Gln Lys Leu Val Phe Phe Ala Glu Asp Val Gly Ser
1               5                   10                  15

Asn Lys Gly Ala Ile Ile Gly Leu Met Val Gly Gly Val Val
            20                  25                  30

<210> SEQ ID NO 28
<211> LENGTH: 30
<212> TYPE: PRT
<213> ORGANISM: Homo sapiens
```

-continued

```
<220> FEATURE:
<221> NAME/KEY: MISC_FEATURE
<222> LOCATION: (1)..(1)
<223> OTHER INFORMATION: Xaa at position 1 is a pyroglutamate residue
<220> FEATURE:
<221> NAME/KEY: PEPTIDE
<222> LOCATION: (1)..(30)
<223> OTHER INFORMATION: peptide sequence from beta-amyloid

<400> SEQUENCE: 28

Xaa Val His His Gln Lys Leu Val Phe Phe Ala Glu Asp Val Gly Ser
 1               5                  10                  15

Asn Lys Gly Ala Ile Ile Gly Leu Met Val Gly Gly Val Val
            20                  25                  30

<210> SEQ ID NO 29
<211> LENGTH: 32
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is a pyroglutamate residue
<220> FEATURE:
<221> NAME/KEY: PEPTIDE
<222> LOCATION: (1)..(32)
<223> OTHER INFORMATION: peptide sequence from beta-amyloid

<400> SEQUENCE: 29

Xaa Val His His Gln Lys Leu Val Phe Phe Ala Glu Asp Val Gly Ser
 1               5                  10                  15

Asn Lys Gly Ala Ile Ile Gly Leu Met Val Gly Gly Val Val Ile Ala
            20                  25                  30

<210> SEQ ID NO 30
<211> LENGTH: 40
<212> TYPE: PRT
<213> ORGANISM: Homo sapiens
<220> FEATURE:
<221> NAME/KEY: MISC_FEATURE
<222> LOCATION: (1)..(1)
<223> OTHER INFORMATION: Xaa at position 1 is a pyroglutamate residue
<220> FEATURE:
<221> NAME/KEY: PEPTIDE
<222> LOCATION: (1)..(40)
<223> OTHER INFORMATION: peptide sequence from beta-amyloid

<400> SEQUENCE: 30

Xaa Phe Arg His Asp Ser Gly Tyr Glu Val His His Gln Lys Leu Val
 1               5                  10                  15

Phe Phe Ala Glu Asp Val Gly Ser Asn Lys Gly Ala Ile Ile Gly Leu
            20                  25                  30

Met Val Gly Gly Val Val Ile Ala
        35                  40

<210> SEQ ID NO 31
<211> LENGTH: 443
<212> TYPE: PRT
<213> ORGANISM: Mus musculus
<220> FEATURE:
<221> NAME/KEY: CHAIN
<222> LOCATION: (1)..(443)
<223> OTHER INFORMATION: Murine Heavy Chain IgG1
```

<400> SEQUENCE: 31

```
Gln Val Gln Leu Gln Gln Pro Gly Ala Glu Leu Val Arg Pro Gly Ala
1               5                   10                  15
Ser Val Lys Leu Ser Cys Lys Thr Ser Gly Tyr Thr Phe Thr Arg Tyr
            20                  25                  30
Trp Ile Asn Trp Val Lys Gln Arg Pro Gly Gln Gly Leu Glu Trp Ile
        35                  40                  45
Gly Asn Ile Arg Pro Ser Asp Ser Tyr Thr Asn Tyr Asn Gln Lys Phe
    50                  55                  60
Lys Asp Lys Ala Thr Leu Thr Val Asp Lys Ser Ser Ser Thr Ala Tyr
65                  70                  75                  80
Met Gln Leu Asn Arg Pro Thr Ser Glu Asp Ser Ala Val Tyr Tyr Cys
                85                  90                  95
Thr Arg Glu Gly Ala Tyr Ser Asp Tyr Glu Thr Tyr Trp Gly Gln Gly
            100                 105                 110
Thr Leu Val Thr Val Ser Ala Ala Lys Thr Thr Pro Pro Ser Val Tyr
        115                 120                 125
Pro Leu Ala Pro Gly Ser Ala Ala Gln Thr Asn Ser Met Val Thr Leu
    130                 135                 140
Gly Cys Leu Val Lys Gly Tyr Phe Pro Glu Pro Val Thr Val Thr Trp
145                 150                 155                 160
Asn Ser Gly Ser Leu Ser Ser Gly Val His Thr Phe Pro Ala Val Leu
                165                 170                 175
Glu Ser Asp Leu Tyr Thr Leu Ser Ser Ser Val Thr Val Pro Ser Ser
            180                 185                 190
Pro Arg Pro Ser Glu Thr Val Thr Cys Asn Val Ala His Pro Ala Ser
        195                 200                 205
Ser Thr Lys Val Asp Lys Lys Ile Val Pro Arg Asp Cys Gly Cys Lys
    210                 215                 220
Pro Cys Ile Cys Thr Val Pro Glu Val Ser Ser Val Phe Ile Phe Pro
225                 230                 235                 240
Pro Lys Pro Lys Asp Val Leu Thr Ile Thr Leu Thr Pro Lys Val Thr
                245                 250                 255
Cys Val Val Val Asp Ile Ser Lys Asp Asp Pro Glu Val Gln Phe Ser
            260                 265                 270
Trp Phe Val Asp Asp Val Glu Val His Thr Ala Gln Thr Gln Pro Arg
        275                 280                 285
Glu Glu Gln Phe Asn Ser Thr Phe Arg Ser Val Ser Glu Leu Pro Ile
    290                 295                 300
Met His Gln Asp Trp Leu Asn Gly Lys Glu Phe Lys Cys Arg Val Asn
305                 310                 315                 320
Ser Ala Ala Phe Pro Ala Pro Ile Glu Lys Thr Ile Ser Lys Thr Lys
                325                 330                 335
Gly Arg Pro Lys Ala Pro Gln Val Tyr Thr Ile Pro Pro Pro Lys Glu
            340                 345                 350
Gln Met Ala Lys Asp Lys Val Ser Leu Thr Cys Met Ile Thr Asp Phe
        355                 360                 365
Phe Pro Glu Asp Ile Thr Val Glu Trp Gln Trp Asn Gly Gln Pro Ala
    370                 375                 380
Glu Asn Tyr Lys Asn Thr Gln Pro Ile Met Asn Thr Asn Gly Ser Tyr
385                 390                 395                 400
Phe Val Tyr Ser Lys Leu Asn Val Gln Lys Ser Asn Trp Glu Ala Gly
                405                 410                 415
```

```
Asn Thr Phe Thr Cys Ser Val Leu His Glu Gly Leu His Asn His His
            420                 425                 430
Thr Glu Lys Ser Leu Ser His Ser Pro Gly Lys
            435                 440
```

ANTIBODIES TO PYROGLUTAMATE AMYLOID-β AND USES THEREOF

This application claims the benefit of U.S. Provisional Application Ser. No. 62/416,788 filed Nov. 11, 2016 which is incorporated by reference in its entirety.

FIELD OF THE INVENTION

This invention relates to the field of antibodies directed to amyloid-beta (Aβ) peptides and therapeutic methods using the antibodies. In particular, antibodies may be used for identifying and treating amyloid-related disorders.

BACKGROUND

Alzheimer's disease (AD) is a degenerative brain disorder characterized clinically by progressive loss of memory, cognition, reasoning, judgment and emotional stability that gradually leads to profound mental deterioration and ultimately death. Alzheimer's disease is a common cause of progressive mental failure (dementia) in the elderly. Alzheimer's disease has been observed worldwide and represents a major public health issue. The disease is currently estimated to affect more than five million individuals in the United States alone. At present it is incurable, and no treatment effectively prevents AD or reverses its symptoms or course.

The brains of individuals with AD exhibit characteristic lesions termed amyloid plaques, amyloid angiopathy (amyloid deposits in blood vessels) and neurofibrillary tangles. Large numbers of these lesions, particularly amyloid plaques and neurofibrillary tangles, are generally found in several areas of the brain important for memory and cognitive function. Amyloid plaques and amyloid angiopathy also characterize the brains of individuals with Trisomy 21 (Down's Syndrome), diffuse Lewy body disease and hereditary cerebral hemorrhage with amyloidosis of the Dutch-type (HCHWA-D).

A major constituent of amyloid plaques is a variety of amyloid-beta (Aβ) peptides that are produced by cleavage of the β-amyloid precursor protein (APP). Deposition of Aβ peptides in brain is hypothesized to be an early and necessary step in the disease cascade leading to AD. The identification of mutations in the amyloid precursor protein and presenillin genes resulting in altered Aβ production and causing familial early onset AD provide strong evidence that altered amyloid metabolism is a central event in the pathogenic process underlying the disease.

Amyloid-β peptides having pyroglutamate at the third residue (3pE Aβ) are a major species deposited in the brain of AD patients. 3pE Aβ is present in almost all diffuse and mature plaques in AD, is metabolically stable and may play a role in both plaque seeding and stabilization (Cynis et al., Molecular Neurodegeneration, 2016; 11:48). Detectable amounts of 3pE Aβ have not been reported in CSF or plasma, thus suggesting that the target peptide is pathology specific (DeMattos et al., Neuron, 2012; 76:1-13). Antibodies that selectively bind to 3pE Aβ may be useful for immunotherapy.

SUMMARY OF THE INVENTION

As embodied and fully described, the invention relates to antibodies and antigen binding fragments thereof that bind to amyloid-β having pyroglutamate at the third residue (3pE Aβ), methods of producing antibodies or antigen binding fragments thereof that bind to 3pE Aβ, assay methods using such antibodies or antigen binding fragments thereof, and use of the antibodies or antigen binding fragments thereof of the invention for the manufacture of a medicament, for treating, delaying the onset of or reversing at least one pathology or symptom of Alzheimer's disease and other β-amyloid-related diseases. Antibodies of the invention preferentially bind Aβ peptide containing 3pE over Aβ peptide that does not contain 3pE.

In particular, the invention relates to an isolated antibody or an antigen binding fragment thereof that binds to 3pE Aβ, comprising a heavy chain of SEQ ID NO:1 and a light chain of SEQ ID NO:12. In other embodiments, the invention relates to an isolated antibody or an antigen binding fragment thereof that binds to 3pE Aβ, comprising a heavy chain variable region of SEQ ID NO:2 and a light chain variable region of SEQ ID NO:13. In other embodiments, the heavy chain variable region comprises CDR1 of any of SEQ ID NOs:3, 6 and 9, CDR2 of any of SEQ ID NOs:4, 7 and 10, CDR3 of any of SEQ ID NOs:5, 8 and 11 and the light variable region comprises CDR1 of any of SEQ ID NOs:14, 17 and 20, CDR2 of any of SEQ ID NOs:15 and 18, CDR3 of any of SEQ ID NO:16 and 19. In a particular embodiment, the heavy chain variable region comprises CDR1, CDR2 and CDR3 of SEQ ID NOs:3-5, respectively and the light chain variable region comprises CDR1, CDR2 and CDR3 of SEQ ID NOs:14-16, respectively. In another particular embodiment, the heavy chain variable region comprises CDR1, CDR2 and CDR3 of SEQ ID NOs:6-8, respectively and the light chain variable region comprises CDR1, CDR2 and CDR3 of SEQ ID NOs:17-19, respectively. In another particular embodiment, the heavy chain variable region comprises CDR1, CDR2 and CDR3 of SEQ ID NOs:9-11, respectively and the light chain variable region comprises CDR1, CDR2 and CDR3 of SEQ ID NOs:20, 18 and 16, respectively.

In a further embodiment, the invention is directed to an isolated antibody or an antigen binding fragment thereof that binds to 3pE Aβ, comprising a heavy chain variable region comprising an amino acid sequence having at least 85%, 90%, 95% or 98% sequence identity with SEQ ID NO:2 and a light chain variable region comprising an amino acid sequence having at least 85%, 90%, 95% or 98% sequence identity with SEQ ID NO:13.

An embodiment of the invention is an isolated antibody or antigen binding fragment thereof comprising a heavy chain variable region having a CDR1 sequence comprising amino acid residues 31-35 of SEQ ID NO:2, a heavy chain variable region having a CDR2 sequence comprising amino acid residues 50-66 of SEQ ID NO:2, a heavy chain variable region having a CDR3 sequence comprising amino acid residues 99-108 of SEQ ID NO:2, a light chain variable region having a CDR1 sequence comprising amino acid residues 24-39 of SEQ ID NO:13, a light chain variable region having a CDR2 sequence comprising amino acid residues 55-61 of SEQ ID NO:13; and a light chain variable region having a CDR3 sequence comprising amino acid residues 94-102 of SEQ ID NO:13.

A preferred embodiment of the invention is an isolated antibody antigen binding fragment thereof comprising a heavy chain variable region CDR1 sequence comprising SEQ ID NO:3, a heavy chain variable region CDR2 sequence comprising SEQ ID NO:4, a heavy chain variable region CDR3 sequence comprising SEQ ID NO:5, a light chain variable region CDR1 sequence comprising SEQ ID NO:14, a light chain variable region CDR2 sequence comprising SEQ ID NO:15, and a light chain variable region CDR3 sequence comprising SEQ ID NO:16.

In preferred embodiments, the antibody described above is a monoclonal antibody. In some preferred embodiments, the antigen binding fragment is selected from the group of fragments consisting of Fv, F(ab'), F(ab')2 and scFv. The antibody or antigen binding fragment thereof selectively binds to 3pE Aβ peptide (e.g., Aβ3pE-40 and Aβ3pE-42), with little or no cross-reactivity to other Aβ peptides or β-amyloid precursor protein (APP).

Embodiments of the invention include a method of generating monoclonal antibodies to 3pE Aβ. A particular embodiment of the invention relates to a hybridoma that produces a monoclonal antibody that binds to 3pE Aβ. In another embodiment, a monoclonal antibody that binds to 3pE Aβ is produced recombinantly. In embodiments, the monoclonal antibodies are expressed by hybridoma cells or are expressed recombinantly. The monoclonal antibodies generated comprise a heavy chain variable region consisting of SEQ ID NO:2 and a light chain variable region consisting of SEQ ID NO:13.

Embodiments of the invention relate to a method of treating Alzheimer's disease and other β-amyloid-related diseases comprising administering the isolated antibody or antigen binding fragment thereof described above that binds to 3pE Aβ to an individual with Alzheimer's disease or other β-amyloid-related disease.

A further embodiment of the invention is a method of clearing plaques associated with Alzheimer's disease or other β-amyloid-related disease comprising administering an isolated antibody or antigen binding fragment thereof described above that binds to 3pE Aβ to an individual with Alzheimer's disease or other β-amyloid-related diseases.

Other embodiments relate to a method of preventing plaque seeding activity of 3pE Aβ comprising administering an isolated antibody or antigen binding fragment thereof described above that binds to 3pE Aβ to an individual with Alzheimer's disease or other β-amyloid-related disease.

Embodiments include a pharmaceutical composition comprising the isolated antibody or antigen binding fragment thereof described above and a pharmaceutically-acceptable carrier. Such pharmaceutical compositions may be administered to a subject with Alzheimer's disease or other β-amyloid-related disease, or used in methods for treating Alzheimer's disease or other β-amyloid-related disease such as the methods described above.

An embodiment includes kits and devices comprising the antibody or antigen binding fragment thereof described above. Further objects, features and advantages of the present invention will be apparent to those skilled in the art from detailed consideration of the preferred embodiments that follow.

BRIEF DESCRIPTION OF THE DRAWINGS

FIG. 1 illustrates amino acid sequences of full-length human (Aβ 1-42) (SEQ ID NO:25), N-truncated (Aβ 3-42) (SEQ ID NO:26), and pyroglutamate-modified (Aβ 3pE-42) (SEQ ID NO:30) Aβ peptides.

FIGS. 6A-6D show cryosections of brains of mice expressing elevated levels of human Aβ42 and Aβ40 after treatment with (A and C) PBS or (B and D) Aβ/pE3/1. (A and B) were stained using only with secondary anti-mouse IgG2a antibody. (C and D) were stained after providing both primary and secondary antibodies. The scale bar represents 2.5 mm.

DETAILED DESCRIPTION OF THE INVENTION

Figure 2A:
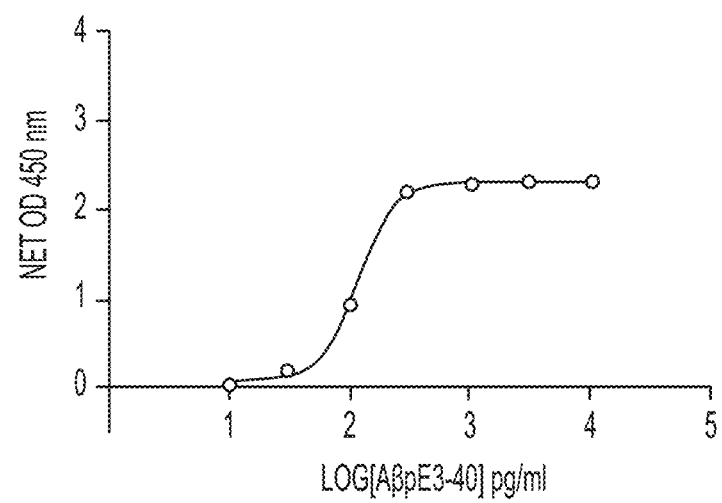
FIGS. 2A-2D shows Aβ/pE3/1 selectivity by detection of synthetic human Aβ peptides in sandwich ELISA. Aβ/pE3/1 bound to (A) Aβ3pE-40 and (B) Aβ3-40 but not to (C) Aβ1-40 and (D) AβpE11-40.

It is to be understood that this invention is not limited to particular methods, reagents, compounds, compositions or biological systems, which can vary. It is also to be understood that the terminology used herein is for the purpose of describing particular embodiments only, and is not intended to be limiting.

The invention provides an antibody or antigen binding fragment thereof that binds to 3pE Aβ peptide, especially preferentially over Aβ peptide that does not contain 3pE. Further provided are methods of producing antibodies or antigen binding fragments thereof that bind to 3pE Aβ peptide, and methods of producing hybridomas which generate antibodies or antigen binding fragments thereof that bind to 3pE Aβ peptide. The invention also includes a method of treating Alzheimer's disease and other β-amyloid-related diseases in an individual, a method of clearing plaques associated with Alzheimer's disease or other β-amyloid-related diseases, and a method of preventing plaque seeding activity of 3pE Aβ. The invention also provides kits and devices comprising the antibody or antigen binding fragment thereof for use in the methods described.

In one embodiment, the present invention is directed to an isolated antibody or a antigen binding fragment thereof which binds to 3pE Aβ, comprising a heavy chain variable region comprising an amino acid sequence having a sequence identity of SEQ ID NO:2, and a light chain variable region comprising an amino acid sequence having a sequence identity of SEQ ID NO:13. In some embodiments, the antibody or antigen binding fragment thereof heavy chain variable region comprises an amino acid sequence having at least 85%, 90%, 95% or 98% sequence identity with SEQ ID NO:2. In other embodiments, the light chain variable region comprises an amino acid sequence having at least 85%, 90%, 95% or 98% sequence identity with SEQ ID NO:13.

An embodiment of the invention is an isolated antibody or antigen binding fragment thereof comprising a heavy chain variable region having a CDR1 sequence comprising amino acid residues 31-35 of SEQ ID NO:2, a heavy chain variable region having a CDR2 sequence comprising amino acid residues 50-66 of SEQ ID NO:2, a heavy chain variable region having a CDR3 sequence comprising amino acid residues 99-108 of SEQ ID NO:2, a light chain variable region having a CDR1 sequence comprising amino acid residues 24-39 of SEQ ID NO:13, a light chain variable region having a CDR2 sequence comprising amino acid residues 55-61 of SEQ ID NO:13; and a light chain variable region having a CDR3 sequence comprising amino acid residues 94-102 of SEQ ID NO:13.

A preferred embodiment is an antibody or antigen binding fragment thereof comprising a heavy chain variable region CDR1 sequence comprising SEQ ID NO:3, a heavy chain variable region CDR2 sequence comprising SEQ ID NO:4, a heavy chain variable region CDR3 sequence comprising SEQ ID NO:5, a light chain variable region CDR1 sequence comprising SEQ ID NO:14, a light chain variable region CDR2 sequence comprising SEQ ID NO:15, and a light chain variable region CDR3 sequence comprising SEQ ID NO:16.

Antibodies

The present invention provides an isolated antibody or antigen binding fragment thereof which binds to 3pE Aβ. The term "antibody" refers herein to an immunoglobulin protein capable of binding an antigen or portion thereof, particularly an immunoglobulin protein capable of specifically binding to 3pE Aβ. Antibody binding to antigen can be measured by methods known to those skilled in the art, an example being the use of a BIAcore™ instrument. Generally speaking, an antibody or antigen-binding antibody fragment, is said to specifically bind an antigen when the dissociation constant is less than or equal to 1 µM, preferably less than or equal to 100 nM and most preferably less than or equal to 10 nM.

Antigen binding fragments of antibodies refers to a fragment of an antibody that can bind to the antigen that the intact antibody binds to and competes with the intact antibody for antigen binding. Antigen binding fragments comprise a portion of an intact antibody that allows for antigen binding (i.e., the variable region of the intact antibody). Antigen binding fragments include Fab, Fab', F(ab')$_2$, and Fv fragments; single-chain antibody molecules (e.g., scFV), diabodies, minibodies, and linear antibodies; and multispecific antibodies formed from antibody fragments.

Antibodies are made up of two heavy chains and two light chains. Each heavy chain has one variable domain or region ($V_H$) followed by a constant domain or region ($C_H1$), a hinge region, and two more constant domains or regions ($C_H2$ and $C_H3$). Each light chain has one variable domain or region ($V_L$) and one constant domain or region ($C_L$). The variable domains or regions of the heavy and light chains form the paratope of the antibody (a structure analogous to a lock), which is specific for a particular epitope (similarly analogous to a key), allowing the paratope and the epitope to bind together with precision. Within the variable domain, variable loops of β-strands, three each on the light and heavy chains, are responsible for binding to the antigen. These loops are referred to as the complementarity determining regions (CDRs, namely CDR1, CDR2, and CDR3).

CDRs are defined as complementarity determining regions of an antibody. These are the hypervariable regions of antibody heavy and light chains that are primarily responsible for binding to the antigen. There are three CDRs (CDR1, CDR2 and CDR3) in each of the heavy and light chain variable regions. The CDRs of an antibody can be defined in a number of ways. For example, the CDRs within the variable region can be identified in accordance with the definitions of the Kabat, Chothia, IMGT and/or conformational definitions or any method of CDR determination well known in the art. Antibody CDRs may be identified as the hypervariable regions originally defined by Kabat (Kabat et al., 1992, Sequences of Proteins of Immunological Interest, 5th ed., Public Health Service, NIH, Washington D.C.), the structural loop structures originally described by Chothia (Chothia et al., Nature 342:877-883 (1989)) or the unique numbering system of IMGT (Lefranc, The Immunologist 7:132-136 (1999); Lefranc, et al., Nucleic Acids Res. 27:209-212 (1999); Scaviner et al., Exp. Clin. Immunogenet. 16:234-240 (1999); Lefranc, et al., Nucleic Acids Res. 43:D413-422 (2015)).

"Isolated" when used in the context of an antibody means altered "by the hand of man" from any natural state; i.e., that, if it occurs in nature, it has been changed or removed from its original environment, or both. For example, a naturally occurring antibody naturally present in a living animal in its natural state is not "isolated", but the same antibody separated from the coexisting materials of its natural state is "isolated", as the term is employed herein. Antibodies may occur in a composition, such as an immunoassay reagent, which are not naturally occurring compositions, and therein remain isolated antibodies within the meaning of that term as it is employed herein.

Methods of producing antibodies comprise inoculating a host with a desired immunogen. Suitable hosts include, but are not limited to, mice, rats, hamsters, guinea pigs, rabbits, chickens, donkeys, horses, monkeys, chimpanzees, orangutans, gorillas, humans, and any species capable of mounting a mature immune response. The immunization procedures are well established in the art and are set forth in numerous treatises and publications including *"The Immunoassay Handbook"*, 2nd Edition, edited by David Wild (Nature Publishing Group, 2000).

Preferably, an immunogen embodying features of the present invention is administered to a host subject, e.g., an animal or human, in combination with an adjuvant. Suitable adjuvants include, but are not limited to, Freund's adjuvant, powdered aluminum hydroxide (alum), aluminum hydroxide together with *Bordetella pertussis*, and monophosphoryl lipid A-synthetic trehalose dicorynomycolate (MPL-TDM).

Typically, an immunogen or a combination of an immunogen and an adjuvant is injected into a mammalian host by one or multiple subcutaneous or intraperitoneal injections. Preferably, the immunization program is carried out over at least one week, and more preferably, over two or more weeks. Polyclonal antibodies produced in this manner can be isolated and purified utilizing methods well know in the art.

Monoclonal antibodies can be produced by the well-established hybridoma methods of Kohler and Milstein, e.g., *Nature* 256:495-497 (1975). Hybridoma methods typically involve immunizing a host or lymphocytes from a host, harvesting the monoclonal antibody secreting or having the potential to secrete lymphocytes, fusing the lymphocytes to immortalized cells, and selecting cells that secrete the desired monoclonal antibody.

A host can be immunized to elicit lymphocytes that produce or are capable of producing antibodies specific for an immunogen. Alternatively, the lymphocytes can be immunized in vitro. If human cells are desired, peripheral blood lymphocytes can be used, although spleen cells or lymphocytes from other mammalian sources are preferred.

The lymphocytes can be fused with an immortalized cell line to form hybridoma cells, a process which can be facilitated by the use of a fusing agent, e.g., polyethylene glycol. By way of illustration, mutant rodent, bovine, or human myeloma cells immortalized by transformation can be used. Substantially pure populations of hybridoma cells, as opposed to unfused immortalized cells, are preferred. Thus, following fusion, the cells can be grown in a suitable medium that inhibits the growth or survival of unfused, immortalized cells, for example, by using mutant myeloma cells that lack the enzyme hypoxanthine guanine phosphoribosyl transferase (HGPRT). In such an instance, hypoxanthine, aminopterin, and thymidine can be added to the medium (HAT medium) to prevent the growth of HGPRT-deficient cells while permitting hybridomas to grow.

Preferably, immortalized cells fuse efficiently, can be isolated from mixed populations by selection in a medium such as HAT, and support stable and high-level expression of antibody following fusion. Preferred immortalized cell lines include myeloma cell lines available from the American Type Culture Collection, Manassas, Va.

One aspect of the invention is a method of producing a hybridoma cell line capable of producing a monoclonal antibody that binds to amyloid beta peptides. Such methods are commonly known to those skilled in the art, and generally comprise: (i) selecting a host for antibody production; (ii) inoculating the host with a desired immunogen; (iii) fusing a cell line from the inoculated host with a continuously dividing cell to create a fused cell capable of producing a monoclonal antibody that binds to the immunogen; and (iv) cloning the fused cell to obtain a hybridoma cell line.

A method of the invention includes producing a hybridoma cell line capable of producing a monoclonal antibody that binds to 3pE Aβ peptide. The hybridoma may be produced by immunizing an animal from which hybridomas can be produced, such as a Balb/c mouse, with initial intraperitoneal injections of the desired immunogens, such as an Aβ peptide having a pyroglutamate, in Freund's adjuvant, followed by booster injections, for example every one to two weeks. The subsequent fusion of the isolated spleen can be carried out using any techniques commonly known to those of ordinary skill in the art, preferably using SP2/0 cells by a modified procedure of Kohler and Milstein (Eur. J. Immunol., 1976; 6:292-295). Screening of the hybridomas to determine those that produce antibodies specific for the 3pE Aβ peptides can be done in a standard assay, such as ELISA or RIA assay. One aspect of the invention is a method of producing a hybridoma cell line that generates the monoclonal antibody Aβ/pE3/1.

Monoclonal antibodies can also be produced by recombinant methods such as are known in the art, e.g., as described in U.S. Pat. No. 4,166,452. DNA encoding monoclonal antibodies can be isolated and sequenced using conventional procedures, e.g., using oligonucleotide probes that specifically bind to murine heavy and light antibody chain genes, preferably to probe DNA isolated from monoclonal antibody hybridoma cells lines secreting antibodies specific for Aβ having a pyroglutamate.

Antibody fragments that contain specific binding sites for amyloid beta peptides may also be generated. Such fragments include, but are not limited to, the F(ab')$_2$ fragments which can be produced by pepsin digestion of the antibody molecule and the Fab fragments which can be generated by reducing the disulfide bridges of the F(ab')$_2$ fragments. Alternatively, Fab expression libraries may be constructed to allow rapid and easy identification of monoclonal Fab fragments with the desired specificity (Huse et al., *Science* 256:1270-1281 (1989)). Fab, Fv and ScFv antibody fragments can all be expressed in and secreted from *Escherichia coli*, allowing for the production of large amounts of these fragments. Alternatively, Fab'-SH fragments can be directly recovered from *E. coli* and chemically coupled to form F(ab')2 fragments (Carter et al., *BioTechnology* 10:163-167 (1992)). Other techniques for the production of antibody fragments are known to those skilled in the art. Single chain Fv fragments (scFv) are also envisioned (see U.S. Pat. Nos. 5,761,894 and 5,587,458). Fv and sFv fragments are the only species with intact combining sites that are devoid of constant regions; thus, they are likely to show reduced non-specific binding. The antibody fragment may also be a "linear antibody" e.g., as described in U.S. Pat. No. 5,642,870, for example.

It is thus an object of the invention to provide isolated monoclonal antibodies expressed by the aforementioned hybridoma cells, the antibodies being capable of specifically recognizing 3pE Aβ. The isolated monoclonal antibodies can be expressed by hybridoma cells or recombinantly.

Preferably, the antibody or antigen binding fragment thereof of the invention binds selectively to 3pE Aβ, with little or no cross-reactivity to other Aβ that do not have 3pE or β-amyloid precursor protein (APP). In particular, the antibody or antigen binding fragment thereof of the invention binds selectively to Aβ 3pE-40 (SEQ ID NO:22) and Aβ 3pE-42 (SEQ ID NO:30) peptides with little or no cross-reactivity to other non-3pE containing Aβ peptides or APP.

Table 1 provides the amino acid sequences of the antibody of the invention. The CDRs of the heavy and light chain variable regions as defined by Kabat, Chothia and IMGT are set forth as separate sequences.

TABLE 1

| Aβ/pE3/1 Antibody Sequences | | |
|---|---|---|
| SEQ ID NO | Description | Sequence |
| 1 | Heavy Chain protein | QVQLQQPGAELVRPGASVKLSCKTSGYTFTRYWINWVKQRPGQGLE WIGNIRPSDSYTNYNQKFKDKATLTVDKSSSTAYMQLNRPTSEDSAV YYCTREGAYSDYETYWGQGTLVTVSAAKTTAPSVYPLAPVCGDTT GSSVTLGCLVKGYFPEPVTLTWNSGSLSSGVHTFPAVLQSDLYTLSSS VTVTSSTWPSQSITCNVAHPASSTKVDKKIEPRGPTIKPCPPCKCPAPN LLGGPSVFIFPPKIKDVLMISLSPIVTCVVVDVSEDDPDVQISWFVNN VEVHTAQTQTHREDYNSTLRVVSALPIQHQDWMSGKEFKCKVNNK DLPAPIERTISKPKGSVRAPQVYVLPPPEEEMTKKQVTLTCMVTDFM PEDIYVEWTNNGKTELNYKNTEPVLDSDGSYFMYSKLRVEKKNWV ERNSYSCSVVHEGLHNHHTTKSFSRTPGK |

TABLE 1-continued

Aβ/pE3/1 Antibody Sequences

| SEQ ID NO | Description | Sequence |
|---|---|---|
| 2 | VH protein | QVQLQQPGAELVRPGASVKLSCKTSGYTFTRYWINWVKQRPGQGLE WIGNIRPSDSYTNYNQKFKDKATLTVDKSSSTAYMQLNRPTSEDSAV YYCTREGAYSDYETYWGQGTLVTVSA |
| 3 | HCDR1 (Kabat) | RYWIN |
| 4 | HCDR2 (Kabat) | NIRPSDSYTNYNQKFKD |
| 5 | HCDR3 (Kabat) | EGAYSDYETY |
| 6 | HCDR1 (Chothia) | GYTFTRY |
| 7 | HCDR2 (Chothia) | RPSDSY |
| 8 | HCDR3 (Chothia) | EGAYSDYET |
| 9 | HCDR1 (IMGT) | GYTFTRYW |
| 10 | HCDR2 (IMGT) | IRPSDSYT |
| 11 | HCDR3 (IMGT) | TREGAYSDYETY |
| 12 | Light Chain protein | DVVMTQTPLTLSVTIGQPASISCKSSQSLLDSNGKTYLNWLLQRPGQ SPKRLIYLVSKLDSGVPDRFTGSGSGTDFTLKISRVEAEDLGVYYCVQ GTHFPFTFGGGTKLEIKRADAAPTVSIFPPSSEQLTSGGASVVCFLNNF YPKDINVKWKIDGSERQNGVLNSWTDQDSKDSTYSMSSTLTLTKDE YERHNSYTCEATHKTSTSPIVKSFNRNEC |
| 13 | VL protein | DVVMTQTPLTLSVTIGQPASISCKSSQSLLDSNGKTYLNWLLQRPGQ SPKRLIYLVSKLDSGVPDRFTGSGSGTDFTLKISRVEAEDLGVYYCVQ GTHFPFTFGGGTKLEIK |
| 14 | LCDR1 (Kabat) | KSSQSLLDSNGKTYLN |
| 15 | LCDR2 (Kabat) | LVSKLDS |
| 16 | LCDR3 (Kabat) | VQGTHFPFT |
| 17 | LCDR1 (Chothia) | SQSLLDSNGKTY |
| 18 | LCDR2 (Chothia) | LVS |
| 19 | LCDR3 (Chothia) | GTHFPF |
| 20 | LCDR1 (IMGT) | QSLLDSNGKTY |
| 18 | LCDR2 (IMGT)[1] | LVS |
| 16 | LCDR3 (IMGT)[2] | VQGTHFPFT |

[1] LCDR2 as defined by IMGT is identical to the LCDR2 as defined by Chothia
[2] LCDR3 as defined by IMGT is identical to the LCDR3 as defined by Kabat Antibodies of the invention also encompass isolated antibodies or antigen binding fragments thereof derived from Aβ/pE3/1 and comprise a heavy chain variable region comprising an amino acid sequence having at least 85%, 90%, 95% or 98% identity with SEQ ID NO:2 and a light chain variable region comprising an amino acid sequence having at least 85%, 90%, 95% or 98% identity with SEQ ID NO:13. In preferred embodiments, the CDRs of dervied antibodies or antigen binding fragments thereof are the same as Aβ/pE3/1.

The term "sequence identity" means that when two amino acid sequences are optimally aligned, a comparison can be made (i.e., on a amino acid residue-by-residue basis) over a comparison window as to how similar they are as measured by well-known algorithms of sequence identity determination such as BLAST, ToPLign, Supermatcher and Matcher.

In Vitro Methods

It is to be understood that all manner of immunoassays employing antibodies or antigen binding fragments thereof are contemplated for use in accordance with the presently preferred embodiments, including assays in which antibodies or antigen binding fragments thereof are bound to solid phases and assays in which antibodies are in liquid media. Methods of immunoassays that can be used to detect analytes using antibodies embodying features of the present invention include, but are not limited to, competitive (reagent limited) assays wherein labeled analyte (analyte analog) and analyte in a sample compete for antibodies and single-site immunometric assays wherein the antibody is labeled; and the like.

The antibodies or antigen binding fragments thereof according to the invention can be used in conventional immunological techniques for the detection of Aβ3pE wherever it may occur, including biological samples for the monitoring of β-amyloid-related diseases and conditioned media from cell culture for monitoring the intracellular processing of APP. Suitable immunological techniques are well known to those skilled in the art and include for example, ELISA, Western Blot analysis, competitive or sandwich immunoassays and the like, as is otherwise well known they all depend on the formation of an antigen-antibody immune complex wherein for the purpose of the assay, the antibody or antigen binding fragment thereof can be detectable labelled with, e.g. radio, enzyme, luminescent or fluorescent labels or it can be immobilized on insoluble carriers. It is thus an object of the invention to provide immunoassays for the determination or detection of Aβ3pE or fragment thereof in a sample, the method comprising contacting the sample with an antibody or antigen binding fragment thereof to Aβ3pE or a fragment thereof according to the invention and determining whether an immune complex is formed between the antibody or antigen binding fragment thereof and the Aβ3pE or fragment thereof. These methods can either be performed on tissue samples or body fluid samples and generally comprise obtaining a sample from the body of a subject; contacting said sample with an imaging effective amount of a detectably labeled antibody or antigen binding fragment thereof according to the invention; and detecting the label to establish the presence of Aβ3pE or fragments thereof in the sample. The measuring methods using the antibodies or antigen binding fragments thereof of the present invention are not particularly limited. Any measuring method may be used as long as the amount of antibodies, antigens or the antigens-antibody complexes corresponding to the amount of the antigens, in particular the amount of Aβ3pE or fragments thereof in solutions to be measured is detected by chemical or physical means, and calculated from standard curves prepared by the use of standard solutions containing the antigens in known amounts. For example, nephelometry, competitive methods, immunometric methods and sandwich methods are suitably used. With respect to sensitivity and specificity, it is particularly preferred to use sandwich methods.

In the sandwich methods, the test solutions are reacted with an insolubilized antibody, such as insolubilized anti-Aβ3pE antibodies (the first reaction), further, the labeled secondary antibodies are reacted (the second reaction); the activity of the labeling agents on the insolubilized carriers is then assayed, whereby the amount of the Aβ3pE or fragments thereof in the test solutions can be determined. The first reaction and the second reaction may be conducted simultaneously or sequentially.

In measuring methods, labelling substances, radioisotopes, enzymes, fluorescent substances, luminous substances, etc. are used as labelling agents. Examples of the radioisotopes include $^{125}I$, $^{131}I$, $^{3}H$ and $^{14}C$. Enzymes are usually made detectable by conjugation of an appropriate substrate that, in turn catalyzes a detectable reaction. Examples thereof include, for example, beta-galactosidase, beta-glucosidase, alkaline phosphatase, peroxidase and malate dehydrogenase, preferably horseradish peroxidase. The luminous substances include, for example, luminol, luminol derivatives, luciferin, aequorin and luciferase. Further, the avidin-biotin systems can also be used for labelling the antibodies and immunogens of the present invention. When the immunogens or antibodies are insolubilized, either physical adsorption or chemical binding usually used for insolubilization or fixation of proteins or enzymes may be employed. Examples of the carriers include insoluble polysaccharides such as agarose, dextran, and cellulose, synthetic resins such as polystyrene, polyacrylamide and silicone polymers, and glass.

In a further embodiment for detecting or diagnosing β-amyloid-related diseases, a biological sample including tissue, body fluids, such as CSF, blood, plasma, serum, urine, and the like, is contained and contacted with a suitable amount of first antibody to produce an immune complex. The contact typically involves adding the sample to a solid matrix coated with the first antibody. The complex which results from contacting the sample with the first antibody is separated from the sample by elution. However, other methods of recovery may be employed. The recovered complex is contacted with at least one second antibody directed to an antigenic determinant on the antigen and capable of binding the antigen in the complex. The antigenic determinant to which the second antibody is directed may be the same one as to which the first antibody is directed due to the multi-epitopic nature of the antigenic entity. Either the first or the second antibody may be made detectable using any of the labels described above. In a preferred embodiment, the second antibody is made detectable. The presence of the detectable antibody bound to the complex consisting of antigen bound to the first and second antibody may be readily detected using art-known techniques. By comparing the results obtained in the biological sample with those obtained on a control sample, the presence of altered Aβ3pE or fragments thereof levels may be determined.

In Vivo Methods

Aspects of the invention relate to a method for preventing, ameliorating, treating and/or decreasing amyloid-beta deposition in amyloid-beta related conditions comprising administration of the antibodies or antigen binding fragments thereof as disclosed herein in a therapeutically effective amount to a subject in need thereof. Additional aspects of the invention include a pharmaceutical composition for preventing, ameliorating, treating and/or decreasing amyloid deposition in amyloid-beta related conditions comprising the antibodies or antigen binding fragments thereof as disclosed herein. Methods of the present invention comprise administering an effective amount of one or more antibodies or antigen binding fragments thereof described herein to a subject in need thereof.

In one aspect, the invention is directed to methods of preventing, ameliorating, treating and/or decreasing amyloid-beta deposition in conditions characterized by the formation of plaques containing beta-amyloid protein in humans, which method comprises administering, preferably peripherally, to a human in need of such treatment a therapeutically or prophylactically effective amount of an antibody according to the invention or immunologically reactive fragment thereof, which antibody specifically binds to human Aβ3pE. In another aspect, the invention is directed to methods of inhibiting the formation of amyloid plaques and/or to clear amyloid plaques in humans, which method comprises administering to a human subject in need of such inhibition or clearing an effective amount of an antibody according to the invention that sequesters Aβ3pE peptide in brain and induces altered Aβ3pE clearance in brain. In additional aspects, the invention is directed to such humanized antibodies, including immunologically effective portions thereof, and to methods for their preparation. In particular embodiments, the humanized antibody has the CDRs of Aβ/pE3/1 (i.e., any of SEQ ID NOs:3-11 and 14-20).

A subject in need thereof is a human suffering or predisposed to suffer from a condition characterized by the formation of plaques containing beta-amyloid protein. In one embodiment, the condition in Alzheimer's disease. In other embodiments, the condition is dementia associated with Trisomy 21 (Down's Syndrome), diffuse Lewy body disease, inclusion body myositis, cerebral amyloid angiopathy or hereditary cerebral hemorrhage with amyloidosis of the Dutch-type (HCHWA-D).

A humanized antibody is an antibody from non-human species whose protein sequences have been modified to increase their similarity to antibody variants produced naturally in humans. Generally, the protein sequence of a humanized antibody is essentially identical to that of a human variant with the exception of the non-human origin of some or all of its complementarity determining regions (CDRs) segments that are responsible for the ability of the antibody to bind to its target antigen. The framework regions of the variable regions are substituted by the corresponding human framework regions leaving the non-human CDR substantially intact. In some cases, humanized antibodies do have a small number of substitutions in one or more of the non-human CDR regions to retain the binding affinity and or dissociation constant of the non-human antibody.

A humanized antibody again refers to an antibody comprising a human framework, at least one CDR from a non-human antibody, and in which any constant region present is substantially identical to a human immunoglobulin constant region, i.e., at least about 85%, 90%, preferably at least 95% identical or 98% identical. Hence, all parts of a humanized antibody, except one or more of the CDRs, are substantially identical to corresponding parts of a human immunoglobulin sequence. For example, a humanized immunoglobulin would typically not encompass a chimeric mouse variable region/human constant region antibody.

Humanized antibodies have at least three potential advantages over non-human and chimeric antibodies for use in human therapy: 1) because the effector portion is human, it may interact better with the other parts of the human immune system (e.g., activate microglia to clear plaques); 2) the human immune system should not recognize the framework or C region of the humanized antibody as foreign, and therefore the antibody response against such an administered antibody should be less than against a totally foreign non-human antibody or a partially foreign chimeric antibody; and 3) administered non-human antibodies have been reported to have a half-life in human circulation that is shorter than the half-life of human antibodies.

In a method to treat and to prevent conditions characterized by the formation of plaques containing beta-amyloid protein, the antibodies or antigen binding fragments thereof (including immunologically reactive fragments) of the invention are administered to a subject at risk for or exhibiting amyloid beta-related symptoms or pathology such as clinical or pre-clinical Alzheimer's disease, dementia associated with Down's syndrome, or clinical or pre-clinical amyloid angiopathy, using standard administration techniques. Preferably, administration is peripherally (i.e. not by administration into the central nervous system) by intravenous, intraperitoneal, subcutaneous, pulmonary, transdermal, intramuscular, intranasal, buccal, sublingual, or suppository administration. Although the antibodies or binding fragments thereof may be administered directly into the ventricular system, spinal fluid, or brain parenchyma, and techniques for addressing these locations are well known in the art, it is not necessary to utilize these more difficult procedures. The antibodies or binding fragments thereof of the invention are effective when administered by the simpler techniques that rely on the peripheral circulation system. The advantages of the present invention include the ability of the antibody or antigen binding fragment thereof to exert its beneficial effects even though not provided directly to the central nervous system itself.

Pharmaceutical compositions for administration are designed to be appropriate for the selected mode of administration, and pharmaceutically acceptable excipients such as dispersing agents, buffers, surfactants, preservatives, solubilizing agents, isotonicity agents, stabilizing agents and the like are used as appropriate. Remington's Pharmaceutical Sciences, Mack Publishing Co., Easton Pa., latest edition, incorporated herein by reference, provides a compendium of formulation techniques as are generally known to practitioners.

It may be particularly useful to alter the solubility characteristics of the antibodies of the invention, making them more lipophilic, for example, by encapsulating them in liposomes or by blocking polar groups.

Peripheral systemic delivery by intravenous or intraperitoneal or subcutaneous injection is preferred. Suitable vehicles for such injections are straightforward. In addition, however, administration may also be effected through the mucosal membranes by means of nasal aerosols or suppositories. Suitable formulations for such modes of administration are well known and typically include surfactants that facilitate cross-membrane transfer. Such surfactants are often derived from steroids or are cationic lipids, such as N-[1-(2,3-dioleoyl)propyl-N,N,N-trimethylammoniumchloride (DOTMA) or various compounds such as cholesterol hemisuccinate, phosphatidyl glycerols and the like.

The concentration of the humanized antibody in formulations from as low as about 0.1% to as much as about 15 or 20% by weight are selected primarily based on fluid volumes, viscosities, and so forth, in accordance with the particular mode of administration selected. Thus, a typical pharmaceutical composition for injection could be made up to contain 1 mL sterile buffered water of phosphate buffered saline and 1-100 mg of the humanized antibody of the present invention. The formulation could be sterile filtered after making the formulation, or otherwise made microbiologically acceptable. A typical composition for intravenous infusion could have a volume as much as 250 mL of fluid, such as sterile Ringer's solution, and 1-100 mg per mL, or more in antibody concentration.

For antibody administration, the dosage ranges from about 0.0001 to 100 mg/kg, and preferably 0.01 to 75 mg/kg, of the host body weight. For example, dosages can be 0.02 mg/kg, 0.25 mg/kg, 0.5 mg/kg, 0.75 mg/kg, 1 mg/kg, 2 mg/kg, 3 mg/kg, 4 mg/kg, 5 mg/kg, 10 mg/kg, 15 mg/kg, 20 mg/kg, 25 mg/kg, 20 mg/kg, 35 mg/kg, 40 mg/kg, 45 mg/kg, 50 mg/kg, 55 mg/kg, 60 mg/kg, 65 mg/kg, 70 mg/kg, or 75 mg/kg of the host body weight. In embodiments, the dosage is within the range of 0.01-10 mg/kg, or within the range of 0.1-15 mg/kg, or within the range of 0.1-20 mg/kg, or within the range of 0.1-30 mg/kg, or within the range of 0.1-40 mg/kg, or within the range of 0.1-50 mg/kg, or within the range of 0.1-60 mg/kg, preferably at least 1 mg/kg, at least 5 mg/kg, at least 10 mg/kg, at least 20 mg/kg, at least 30 mg/kg, at least 40 mg/kg, at least 50 mg/kg or at least 60 mg/kg. In a preferred example, dosages can be about 10 kg/mg, about 20 kg/mg, about 30 kg/mg, about 40 mg/kg, about 50 mg/kg, about 60 mg/kg or about 70 mg/kg. In a particularly preferred example, the antibody is administered intraperitoneally at a dose range from about 0.3 mg/kg to about 60 mg/kg. In an exemplary treatment regime, the antibody is administered intraperitoneally at a dosage about 10 kg/mg, about 20 kg/mg, about 30 kg/mg, about 40 mg/kg, about 50 mg/kg or about 60 mg/kg.

As used herein, the term "about" when referring to a measurable value such as an amount is meant to encompass variations of between ±20% and ±0.1%, preferably ±15% or ±10%, more preferably ±5%, even more preferably ±1%, and still more preferably ±0.5%, ±0.1%. ±0.05% or ±0.01% of the specified value, as such variations are appropriate.

An exemplary treatment regime entails administration once per every two weeks or once a month or once every 3 to 6 months. In some methods, two or more monoclonal antibodies with different binding specificities are administered simultaneously, in which case the dosage of each antibody administered falls within the ranges indicated. Antibody is usually administered on multiple occasions. Intervals between single dosages can be weekly, monthly or yearly. Intervals can also be irregular as indicated by measuring blood levels of antibody to Aβ in the subject. Alternatively, antibody can be administered as a sustained release formulation, in which case less frequent administration is required. Dosage and frequency vary depending on the half-life of the antibody in the patient. In general, human antibodies show the longest half-life, followed by humanized antibodies, chimeric antibodies, and nonhuman antibodies.

The dosage and frequency of administration can vary depending on whether the treatment is prophylactic or therapeutic. In prophylactic applications, a relatively low dosage is administered at relatively infrequent intervals over a long period of time. Some subjects continue to receive treatment for the rest of their lives. In therapeutic applications, a relatively high dosage at relatively short intervals may be required until progression of the disease is reduced or terminated, and preferably until the subject shows partial or complete amelioration of symptoms of disease. Thereafter, a prophylactic regime can be administered.

In some methods, the dosage is administered to achieve a plasma antibody concentration of 1-1000 μg/ml, and in some methods 25-300 μg/ml. Alternatively, antibody can be administered as a sustained release formulation, in which case less frequent administration is required. Dosage and frequency vary depending on the half-life of the antibody in the subject.

Treatment with an antibody of the invention may be a stand-alone treatment. Alternatively, treatment with an antibody of the invention may be one component or phase of a combination therapy regime, in which one or more additional therapeutic agents are also used to treat an individual.

When used for in vivo therapy, the antibodies or antigen binding fragments thereof of the invention are administered to the individual in therapeutically effective amounts, e.g., amounts which reduce, clear or prevent β-amyloid plaques or improve cognitive function in subjects with AD or other β-amyloid-related diseases. The antibodies or antigen binding fragments thereof are administered to an individual, in accord with known methods, such as intravenous administration, e.g., as a bolus or by continuous infusion over a period of time, by intramuscular, intraperitoneal, intracerobrospinal, subcutaneous, intra-articular, intrasynovial, intrathecal, oral, topical, or inhalation routes. Agents of the invention can optionally be administered in combination with other agents that are at least partly effective in treatment of amyloidogenic disease. In the case of Alzheimer's and related conditions in which amyloid deposits occur in the brain, antibodies or antigen binding fragments thereof of the invention can be administered in conjunction with other agents that increase passage of the agents of the invention across the blood-brain barrier.

In an embodiment of the invention, antibodies or antigen binding fragments thereof of the invention bind to 3pE Aβ in plaque deposits. By binding to 3pE Aβ in plaque deposits, the antibody or antigen binding fragment thereof can induce plaque removal. Induction of plaque removal may be by activation of microglia around plaques and by destabilizing plaques by removing a stable Aβ form. Moreover, antibodies or antigen binding fragments thereof of the invention may prevent plaque seeding activity of 3pE Aβ. The possible enrichment of 3pE Aβ in plaque compared to vascular amyloid may increase the therapeutic safety window for immunotherapy.

Kits and Devices

The present invention provides kits and devices that can be used in the above-mentioned methods. Preferably, the kits and devices comprise an antibody or antigen binding fragment thereof that binds to 3pE Aβ. In addition, the kits may comprise reagents and instructional materials. Instructions may be printed, e.g., on paper and/or supplied in an electronically-readable medium. Alternatively, instructions may be provided by directing a user to an internet website, e.g., specified by the manufacturer or distributor of the kit.

Reagents included in kits of the present invention can be supplied in all manner of containers such that the activities of the different components are substantially preserved while the components themselves are not substantially adsorbed or altered by the materials of the container.

In one embodiment, a kit or device comprises an antibody or antigen binding fragment thereof of the invention, preferably a purified antibody, more preferably a monoclonal antibody, even more preferably the isolated monoclonal antibodies that bind to 3pE Aβ peptides. In embodiments, the antibodies are expressed by the hybridoma cells.

EXAMPLES

The invention can be further understood in view of the following non-limiting examples.

Example 1

Generation of Monoclonal Antibodies

Three Balb/c mice (Janvier Labs) were primed with H2N-pEFRHDSGC-COOH (SEQ ID NO:21) (Eurogentec) in complete Freund's adjuvant (Sigma). The peptides were prepared by coupling the peptides via a COOH-terminal cysteine residue to Maleimide Activated Bovine Serum Albumin (Life Technologies) using commercially available kits such as the Imject Maleimide Activated BSA kit (Pierce, Rockford, Il.), according to the manufacturer's instructions. The mice were boosted every two weeks with 100 µg or 200 µg BSA-coupled peptide, first in complete and subsequently in incomplete Freund's adjuvant (Sigma).

Hybridoma and Antibody Production: The mouse showing the highest serum titer was selected for fusion while the spleens of the other mice were isolated and frozen in liquid nitrogen. On day 4, before fusion or spleen extraction, all mice were boosted intraperitoneally with 100 µg of pEFRHDSGC (SEQ ID NO:21) coupled to BSA (Merck) in saline. Mouse spleen cells were fused with SP2/0 cells (ATCC, Manassas, Va.) by a modified procedure of Kohler and Milstein (*Euro. J. Immunol.*, 1976; 292-295). The hybridomas were seeded in 30×96-well plates and screened after 10 days in a direct ELISA on 0.5 µg/well non-coupled Aβ 3pE-40 peptide (SEQ ID NO:22) (AnaSpec, Fremont, USA). Positive cells were tested for (lack of) cross-reactivity on 0.5 µg/ml coated Aβ1-40 peptide (SEQ ID NO:23) (AnaSpec, Fremont, USA) and were immediately subcloned.

After the first fusion, 17 clones reacted as positive in a directly coated ELISA screen with human Aβ3pE-40 (SEQ ID NO:22) synthetic peptide and were frozen in liquid nitrogen. The 17 clones were named Aβ/pE3/1 to Aβ/pE3/7. A second fusion was performed and 2 other clones from this second fusion were also included in further characterizations (Aβ/pE3/1 8 and Aβ/pE3/1 9).

All hybridomas were grown in Dulbecco's modified Eagle's medium supplemented with 10% fetal calf serum (Hyclone, Europe), Hybridoma Fusion Cloning Supplement (2%) (Roche, Brussels, Belgium), 2% HT (Sigma, USA), 1 mM sodium pyruvate, 2 mM L-glutamine and penicillin (100 U/ml) and streptomycin (50 mg/ml). All products were commercially available and purchased from Life Technologies (Paisley, UK). Cells were incubated in a humidified 8% $CO_2$ air incubator.

Direct ELISA for Antibody selection: The screening ELISA used for the detection of Aβ 3pE-40 antibodies above was a direct ELISA with 0.5 µg/ml free human Aβ 3pE-40 peptide (SEQ ID NO:22) coated overnight at 4° C. in NUNC Maxisorp (Life Technologies) flat-bottom high-binding 96-well microtiter plates in 50 µl/well coating buffer (10 mM Tris, 10 mM NaCl, and 10 mM $NaN_3$, pH 8.5).

The next day, the plates were blocked with 75 µl/well of 0.1% casein (Merck) in PBS for 60 min at room temperature to reduce non-specific binding. Next, 50 µl hybridoma supernatant was added and incubated for 1 h at 37° C. After washing, the bound monoclonal antibodies were detected with 50 µl/well of sheep-anti-mouse IgG conjugated with horseradish peroxidase (Amersham-Pharmacia Biotech) for 1 hr at 37° C. Both reagents were diluted in 0.1% casein/PBS. The plates were washed and 50 µl of a solution of 0.42 mM 3,5,3',5'-tetramethyl-benzidine (Biorad), 0.003% (vol/vol) $H_2O_2$ (Biorad) in 100 mM citric acid (Biorad); 100 mM disodium hydrogen phosphate (pH 4.3) (Biorad) was added as the substrate. The reaction was allowed to proceed for maximum 15 min on a plate shaker at room temperature, after which the colour development was stopped with 2 N $H_2SO_4$ (Merck) 50 µl/well and the plates were read on a microtiter plate reader at 450 nm (Thermomax, Molecular Devices). The cross-reactivity of the selected monoclonal antibodies with full-size human free Aβ 1-40 (SEQ ID NO:23) was tested in a direct ELISA, identical to the screening assay.

Aβ/pE3/1 was determined to have a murine IgG1 isotype heavy chain and a murine kappa light chain. Although the murine IgG1 Fc has only 70% sequence identity and 76% sequence similarity to the murine IgG2a Fc, these isotypes have different activities and protein profiles. Compared to murine IgG2a, murine IgG1 has less murine Fc effector and complement function because of weaker binding to murine FcγRI, FcγRIII, and FcγRIV receptors and murine C1q. Considered to be the isotype that is closest to human IgG1 activity, murine IgG2a binds to murine FcγRI, FcγRIII, and FcγRIV receptors and murine C1q thereby having complement, ADCC, and ADCP activity that can contribute to the clearance of Aβ plaques.

The sequence of Aβ/pE3/1 heavy chain was altered from murine IgG1 (SEQ ID NO:31) to murine IgG2a (SEQ ID NO:1). Experimental data described infra used Aβ/pE3/1 with an IgG2a heavy chain. The heavy chain variable region (including CDRs) was not altered.

Example 2

Sandwich ELISA for Sensitivity Testing

For the selected Aβ 3pE monoclonal antibodies, the sensitivity for detection of Aβ3-40 (SEQ ID NO:24) (AnaSpec, Fremont, USA) and Aβ3pE-40 (SEQ ID NO:22) (AnaSpec, Fremont, USA) was evaluated in a sandwich assay using synthetic peptides as standards. The combination Aβ/pE3/1-19 antibodies for coating and JRF/cAβ40/28-HRPO for detection was used to investigate sensitivity of detection.

Material and methods: Standards of Aβ3-40 (SEQ ID NO:24) and Aβ3pE-40 (SEQ ID NO:22) peptides were dissolved in dimethylsulphoxide (DMSO) (Sigma) at 0.1 mg/mL and stored at −80° C. For use in ELISA, peptides were further diluted in 0.1% casein in PBS down to 1 pg/mL. Ninety six-well-plates (half-area black plates; Costar) were coated overnight at 4° C. with monoclonal antibodies Aβ/pE3/1-Aβ3/pE3/9 at a concentration of 1.5 µg/mL in coating buffer. The next day, plates were washed and blocked with 0.1% casein in PBS for 1-4 hours at room temperature. Standards were incubated overnight at 4° C. together with HRPO-labeled secondary antibody. After overnight incubation, the plates were washed and the assay was developed with Quantablu substrate (Pierce, Rockford, Ill.) according to the manufacturer's recommendations.

Results: Antibody Aβ/pE3/1 was selected for further characterization based on high sensitivity and selectivity for Aβ3pE-40 (SEQ ID NO:22) peptide (Table 2). Furthermore, this antibody demonstrated plaque labelling on transgenic mouse and human AD brain (Table 2, and Examples 5 and 6).

TABLE 2

| Clone | Subtype | Sandwich ELISA test for reactivity (EC50; nM) | | Immunohistochemistry with purified monoclonal antibodies (transgenic mouse brain) |
|---|---|---|---|---|
| | | Aβ 3pE-40 | Aβ3-40 | Binding to Plaques |
| 1 | IgG2a, kappa | 0.026 | 0.355 | +++ |
| 2 | IgG1, kappa | 0.036 | 0.561 | +++ |
| 4 | IgG1, kappa | 0.025 | 0.331 | ++ |
| 5 | IgG1, kappa | 0.027 | 0.362 | ++ |
| 6 | IgG1, kappa | NA | NA | +/− |
| 7 | IgG2$_b$, kappa | 0.056 | 0.679 | + |
| 8 | IgG2$_b$, kappa | NA | NA | +/− |
| 10 | IgG2$_b$, kappa | 0.364 | NA | +/− |
| 11 | IgG1, kappa | NA | NA | +/− |
| 12 | IgG1, kappa | 0.077 | 1.052 | + |
| 14 | IgG2$_a$, kappa | 0.091 | 1.148 | ++ |
| 15 | IgG1, kappa | NA | NA | +/− |
| 16 | IgG1, kappa | 0.024 | 0.326 | ++ |
| 17 | IgG2$_a$, kappa | 0.077 | 0.691 | + |
| 18 | IgG1, kappa | NA | NA | +/− |
| 19 | IgG1, kappa | NA | NA | +/− |

Example 3

Sandwich ELISA for Cross-Reactivity Testing

For the selected Aβ3pE monoclonal antibody Aβ3/pE3/1, the cross-reactivity with rodent Aβ3pE-40 and human Aβ1-40 (SEQ ID NO:23), Aβ3-40 (SEQ ID NO:24), Aβ1-42 (SEQ ID NO:25), Aβ3-42 (SEQ ID NO:26), Aβ11pE-40 (SEQ ID NO:28) and Aβ11pE-42 (SEQ ID NO:29) was evaluated using synthetic peptides. The combination Aβ/pE3/1+JRF/cAβ40/28-HRPO was used to investigate the cross-reactivity with Aβ1-40 (SEQ ID NO:23), Aβ3-40 (SEQ ID NO:24), Aβ11pE-40 and rodent Aβ3pE-40. The combination Aβ/pE3/1+JRF/cA1342/26-HRPO was used to investigate the cross-reactivity with Aβ1-42 (SEQ ID NO:25), Aβ11pE-42 and Aβ3-42 (SEQ ID NO:26). Concentrations up to 10,000 pg/mL were tested.

Materials and Methods: Standards were dissolved in dimethylsulphoxide (DMSO) (Sigma) at 0.1 mg/mL and stored at −80° C. For use in ELISA, peptides were further diluted in 0.1% casein in PBS down to 1 pg/mL. Ninety six-well-plates (Maxisorb ELISA plates; NUNC) were coated overnight at 4° C. with monoclonal antibodies from Aβ/pE3/1 at a concentration of 1.5 μg/mL in coating buffer. The next day, plates were washed and blocked with 0.1% casein in PBS for 1-4 hours at room temperature. Standards were incubated overnight at 4° C. together with HRPO-labeled secondary antibody (JRF/cAβ40/28-HRPO or JRF/cAβ42/26-HRPO). After overnight incubation, plates were washed and the assay was developed with TMB peroxide EIA substrate kit (Biorad) according to the manufacturer's recommendations.

Figure 2B:
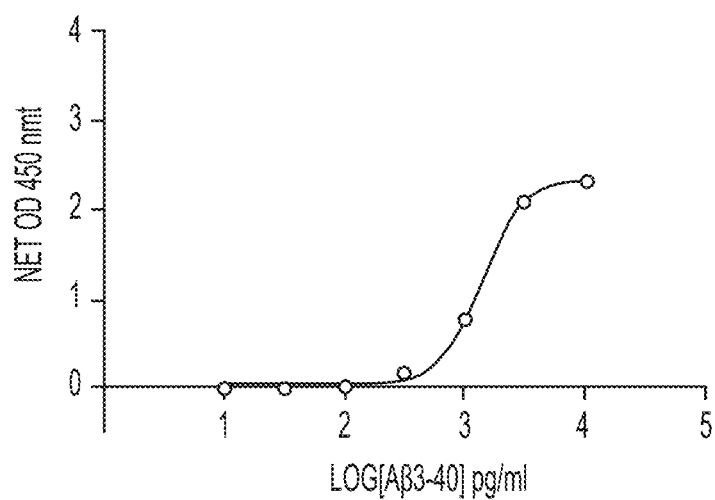
Figure 2C:
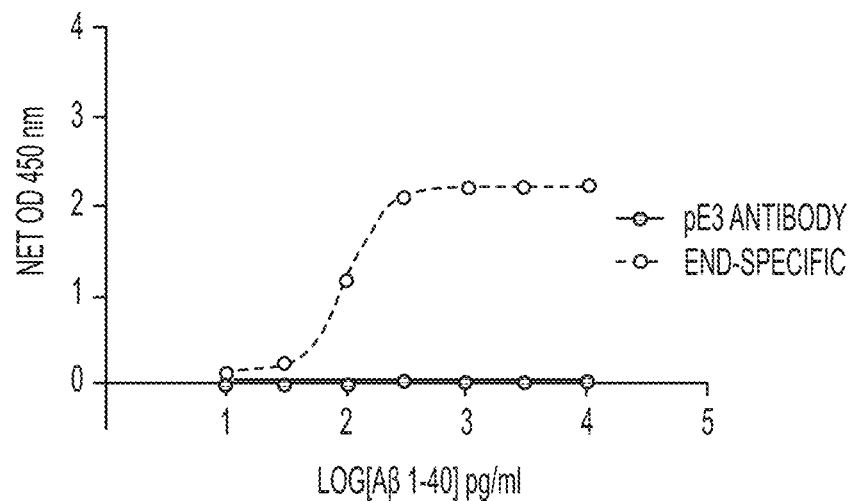
Figure 2D:
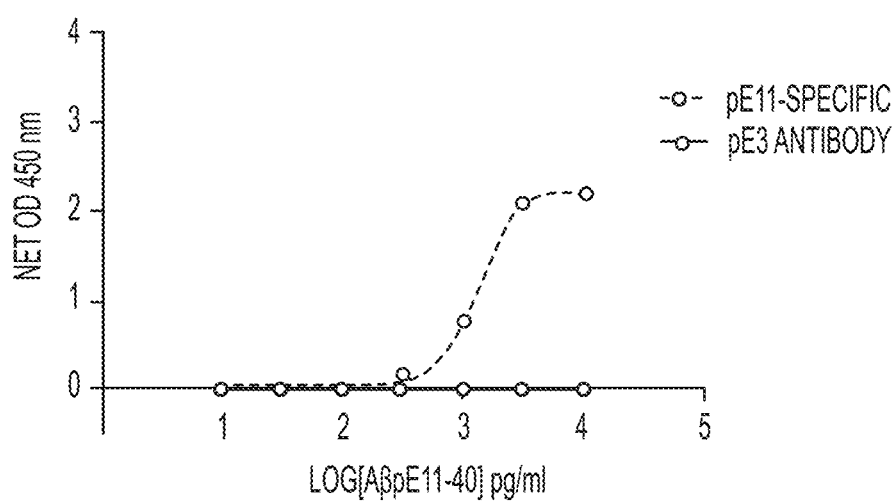

Results: Aβ/pE3/1 Aβ/pE3/1 was shown to have selective binding to Aβ3pE-40 (SEQ ID NO:22) (FIG. 2A) and Aβ3pE-42 (SEQ ID NO:30) (data not shown). No binding was detected to human Aβ1-40 (SEQ ID NO:23) (FIG. 2C) and AβpE11-40 (FIG. 2D). No binding was also detected to human Aβ1-42 (SEQ ID NO:25), human Aβ3pE11-42 and rodent Aβ3pE-40 and at concentrations up to 10 ng/mL (data not shown). Limited crossreactivity was detected for Aβ3-40 (SEQ ID NO:24) (FIG. 2B) and Aβ3-42 (SEQ ID NO:26) (data not shown) peptides (Table 2 and FIG. 2).

Example 4

Immunohistochemistry for Testing Antibody Reactivity to Plaques in Human AD Brain Tissue Reactivity of Aβ/pE3/1 to plaques in human AD brain tissue was investigated both in formalin-fixed, paraffin-embedded (FFPE) as well as non-fixed cryopreserved brain tissue.

Materials and Methods

Formalin fixed paraffin embedded AD brain: Sections of 6 μm thickness were prepared from formalin-fixed, paraffin-embedded brains using a microtome (Leica, Wetzlar, Germany). Staining was performed on Labvision Autostainer (Thermo Fisher Scientific, Fremont, Calif.). Briefly, after deparaffination and 70% formic acid (Merck) epitope retrieval, sections were blocked for endogenous peroxidase and incubated with Aβ/pE3/1 primary antibody. Secondary anti-mouse or anti-rabbit antibody conjugated to HRPO was applied (Envision) and 3,3'-diaminobenzidine (DAB; Dako) was utilized as a chromogen. Finally, all sections were counterstained with hematoxylin (Dako).

Figure 4A:
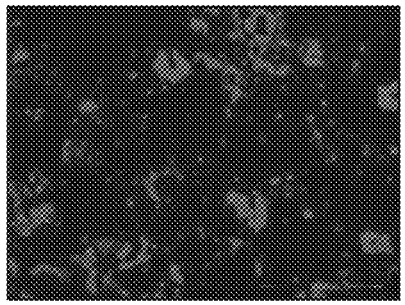
FIGS. 4A-4D show reactivity to plaques in non-fixed cryopreserved AD brain tissue by immunohistochemistry by (A-B) Aβ/pE3/1 and (C-D) positive control polyclonal antibody. Two different views of the same stained brain section are shown for each.
Figure 4B:
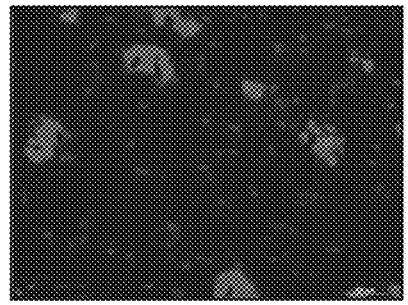
Figure 4C:
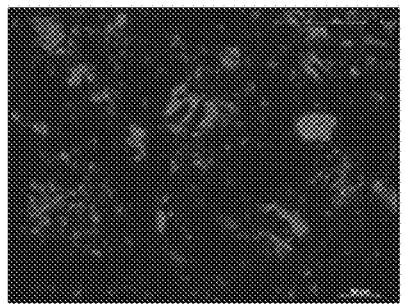
Figure 4D:
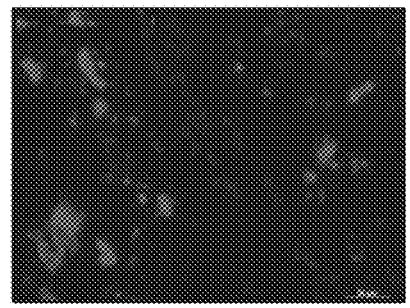

Non-fixed cryopreserved AD brain: Sections were obtained from a commercial source (T1236051A1z-sections, Gentaur) and air-dried for 2 hours at room temperature. After rinsing in PBS, sections were incubated with the Aβ/pE3/1 primary antibody at 37° C. Next sections were fixed in NBF 4% (formalin, VWR®)/ethanol and rinsed in PBS. Secondary Cy3-labelled antibodies (Jackson-ImmunoResearch), were incubated for 2 hours at room temperature, followed by rinsing in PBS. Finally, all sections were counterstained with Hoechst (Invitrogen), and cover slips were added. Two different views of the stained brain section were captured for the Aβ/pE3/1 stained section (FIGS. 4A-4B) and the positive control stained section (FIGS. 4C-4D).

For the immunohistochemistry test of Aβ/pE3/1 for reactivity to plaques in FFPE and cryopreserved AD brain tissue, the polyclonal antibody was used as a control.

Figure 3A:
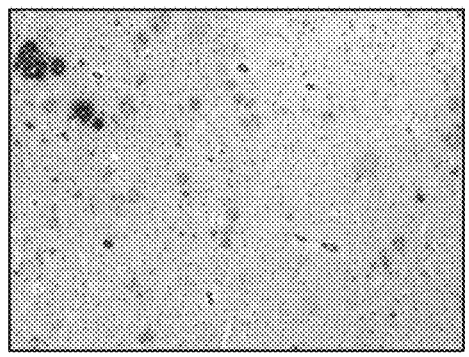
FIGS. 3A-3B show reactivity to plaques in formalin-fixed, paraffin-embedded (FFPE) AD brain tissue by immunohistochemistry by (A) Aβ/pE3/1 and (B) positive control polyclonal antibody.
Figure 3B:
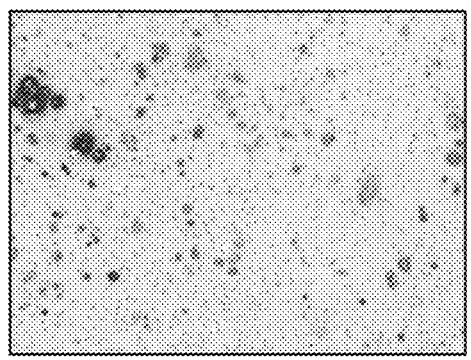

Results: Reactivity of Aβ/pE3/1 was demonstrated on both FFPE (FIG. 3A) and unfixed cryopreserved (FIGS. 4A-4B) human AD brain, displaying a similar staining pattern as a reference antibody (anti-human amyloidβ (N3pE) rabbit IgG, IBL, Japan) (FIGS. 3B and 4C-4D). This demonstrated that Aβ/pE3/1 detected plaques in human brain tissue.

Example 5

Target Engagement and Toxicity of Antibody in Brain Tissue

Target engagement and toxicity after treatment with Aβ/pE3/1 (antibody from clone 1) was investigated.

Material and methods: Aged transgenic mice expressing elevated levels of human Aβ42 and Aβ40 peptides (19-20 months old) were treated with 3 i.p. doses of 60 mg/kg of Aβ/pE3/1 (clone 1) antibodies (IgG2a) on day 1, 4 and 8 (n=10). A control group receiving PBS injection was included in the experiment (n=6). Animals were euthanized on day 12 after the first injection. Half of the treated mice in each group received perfusion with PBS, while the other half was non-perfused to allow the evaluation of potential abnormalities at autopsy. The left hemisphere was cryopreserved, while the right hemisphere was fixed in DMFA, followed by paraffin embedding.

Transgenic mice expressing elevated levels of human Aβ42 and Aβ40 peptides at 6 months old were treated with a single i.p. dose of 20 mg/kg or 60 mg/kg Aβ antibody 3D6 (IgG2a; binds to N terminus of Aβ) on day 1 (n=4 per group). At this age, animals are known to have substantial Aβ deposition in brain. A control group receiving PBS injection was included in the experiment (n=3). Animals were euthanized on day 4. Mice did not receive perfusion to allow the evaluation of potential abnormalities at autopsy.

To evaluate target engagement in the brain after systemic administration of antibody, immunohistochemistry with a secondary anti-mouse isotype-specific antibody (biotinylated anti-mIgG2a secondary antibody; Life Technologies) was performed on cryosections from perfused mice and % of labelled area (cortex and hippocampus) was normalized to the same measure on adjacent sections incubated with primary and secondary antibody to obtain % plaque labelling for each mouse.

To evaluate potential toxicity, hemorrhages at autopsy were evaluated in the groups of non-perfused animals. Additionally, hematoxylin and eosin (H&E) staining was performed on brains of all treated mice.

Figure 5A:
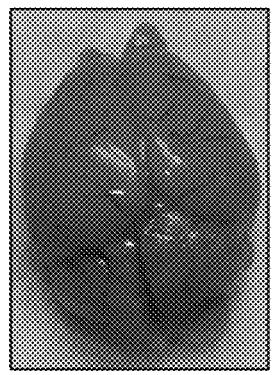
FIGS. 5A-5O show representative images of brains in mice that were treated with Aβ antibodies or control. Three different brains are shown for each treatment of six month old mice with (AC) PBS; (D-F) end-specific Aβ antibody 3D6 (60 mg/kg) or (H-J) 3D6 (20 mg/kg). Two or three different brains are shown for each treatment of nineteen to twenty month old mice with (K-L) PBS; or (M-O) Aβ/pE3/1 (60 mg/kg). Arrows indicate observation of hemorrhages at autopsy.
Figure 5B:
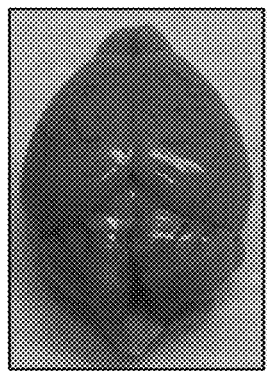
Figure 5C:
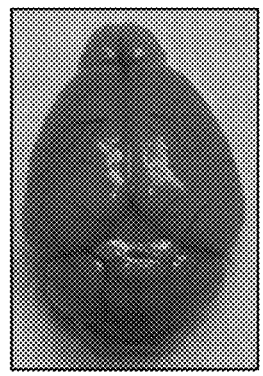
Figure 5D:
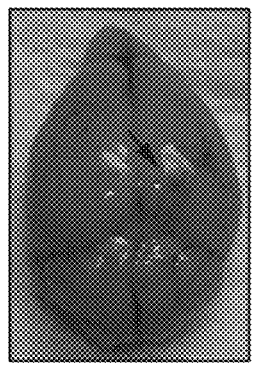
Figure 5E:
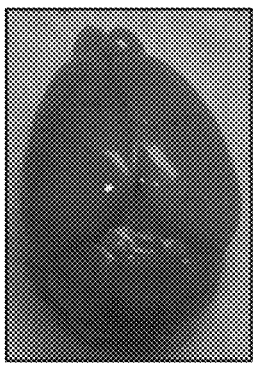
Figure 5F:
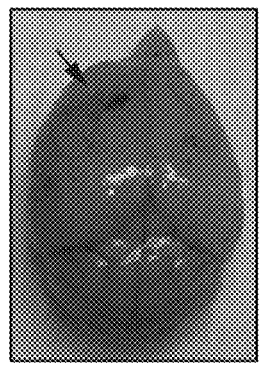
Figure 5H:
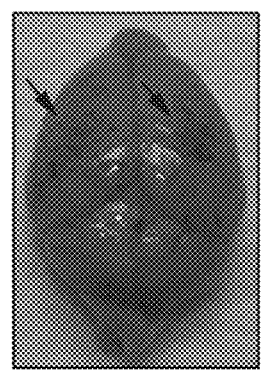
Figure 5I:
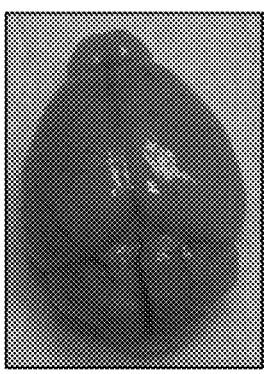
Figure 5J:
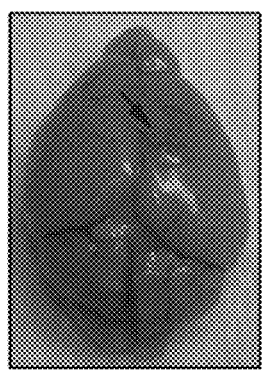
Figure 5K:
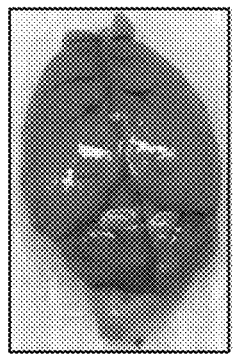
Figure 5L:
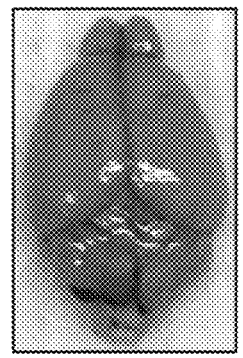
Figure 5M:
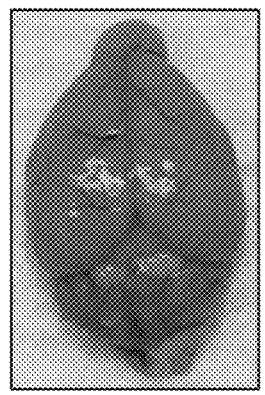
Figure 5N:
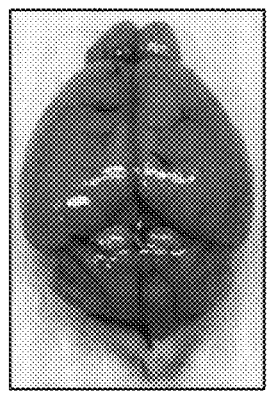
Figure 5O:
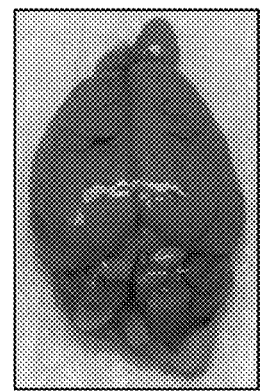

Results: Target engagement (plaque binding) and no toxicity after treatment with 3 doses of 60 mg/kg of the antibody from Aβ/pE3/1 was observed in 19-20 month old mice expressing elevated levels of human Aβ42 and Aβ40. In non-perfused animals, no hemorrhages were observed at autopsy (FIGS. 5M-5O). After treatment with a single dose of 20 mg/kg or 60 mg/kg antibody 3D6, hemorrhages were readily observed at autopsy in 75% of the treated mice expressing elevated levels of human Aβ42 and Aβ40 (6 months old) (FIGS. 5D-5F and 5H-5J, indicated by arrows). None of the animals in the PBS-treated groups showed hemorrhages at autopsy (FIGS. 5A-C and 5K-5L). Two or three different brains are shown for each treatment group.

Investigation of cryosections from Aβ/pE3/1-treated mice revealed a high level of target engagement as demonstrated by a mean % plaque labelling in cortex of 60% and in hippocampus of 84% (FIG. 6B). No plaque labelling was observed in PBS injected-animals (FIG. 6A). As a control, primary antibody (Aβ/pE3/1) was added to parallel sections of brain and staining with secondary antibody to show the presence of plaques in both brains (PBS and Aβ/pE3/1-treated) (FIGS. 6C-6D).

Figure 7A:
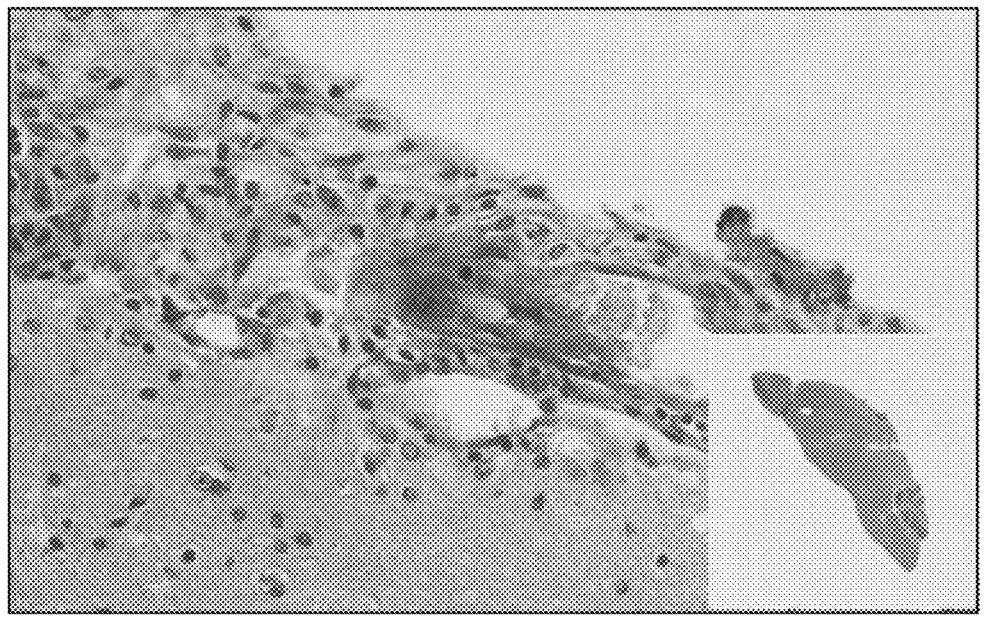
FIGS. 7A-7C show staining with hematoxylin and eosin (H&E) after treatment with (A) 3D6 antibody, (B) Aβ/pE3/1 or (C) PBS in 6 month or 19-20 month old mice expressing elevated levels of human Aβ42 and Aβ40.
Figure 7B:
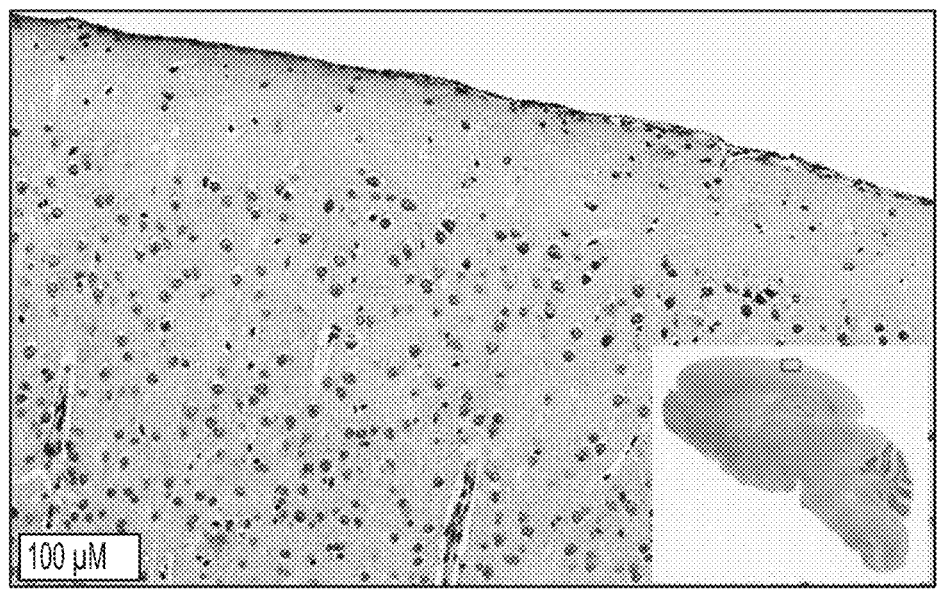
Figure 7C:
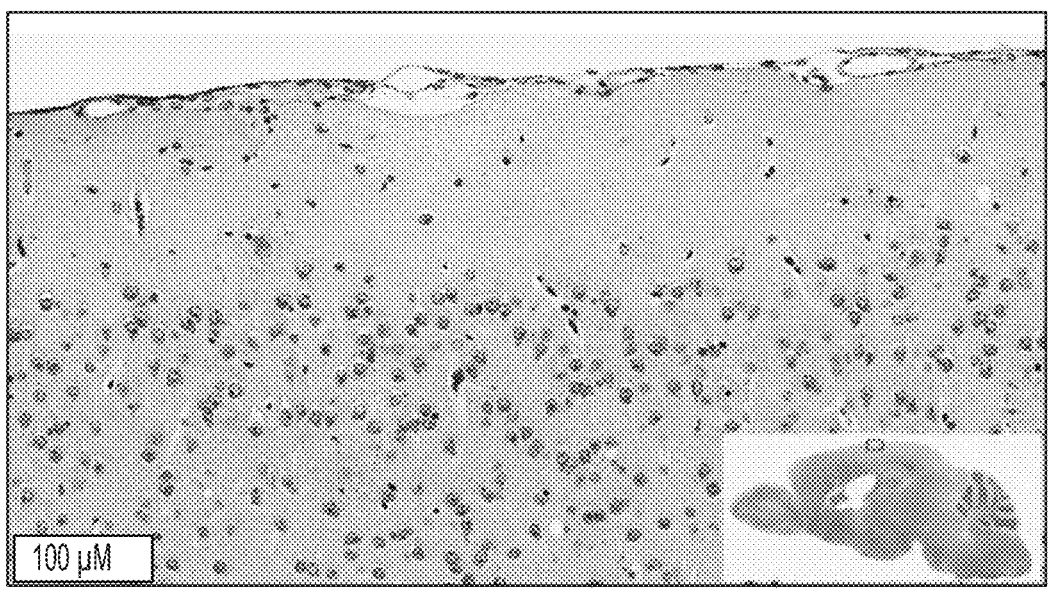

Upon evaluation of brain tissue with H&E staining, mice treated with Aβ/pE3/1 demonstrated no abnormalities (FIG. 7B) as compared to PBS-injected controls (FIG. 7C). Treatment with 3D6 antibody on the other hand, resulted in the observation of the following abnormalities: degeneration/necrosis in cortex (20% and 40% of 3D6-treated mice in 20 mg/kg and 60 mg/kg group, respectively), meningeal inflammatory infiltrate with congestion and micro-angiopathy (100% and 80% of 3D6-treated mice in 20 mg/kg and 60 mg/kg group, respectively) and cortical microhemorrhages (60% of 3D6-treated mice in both 20 mg/kg and 60 mg/kg group, respectively) (FIG. 7A). None of the animals in the PBS-treated groups showed abnormalities on H&E-stained brain slides (FIG. 7C). Aβ/pE3/1 and PBS treated mice were 19-20 months old while 3D6 treated mice were 6 months old.

In conclusion, target engagement was demonstrated without causing hemorrhages after i.p. injection with Aβ/pE3/1 in a plaque-depositing mouse model, indicating a favorable ratio of target engagement versus toxicity after treatment with Aβ/pE3/1 antibody.

Example 6

Biomolecular affinity binding of Aβ/pE3/1

Surface Plasmon Resonance (SPR) is a label-free detection method used to investigate biomolecular interactions. Monitoring small changes in mass on a sensor surface, this direct real-time binding assay provides qualitative and quantitative data about the interaction between biomolecules; i.e. determination of equilibrium binding constant (affinity, $K_D$) and kinetic rate constants ($k_a/k_d$; rate of complex association $k_a$, and rate of complex dissociation $k_d$). This method is useful in studies of protein-protein and protein-nucleic acid interactions, as well as interactions between proteins and small molecules. Here, interactions between Aβ/pE3/1 and Aβ-3pE-40 peptide were investigated.

Materials and Methods: A mouse antibody capture kit from GE Healthcare was used for the affinity study of Aβ/pE3/1 against the Aβ-3pE-40 peptide (SEQ ID NO:22). Immobilization of the anti-mouse antibody was performed via amine coupling on a CM5 sensor chip following the manufacturer's protocol. Subsequently, Aβ/pE3/1 (1 µg/ml) was captured by the anti-mouse antibody to a level of 300 RU, followed by injection of human Aβ 3pE-40 peptide (SEQ ID NO:22) at various concentrations (3.125 nM, 6.25 nM, 12.5 nM, 25 nM and 50 nM) diluted in running buffer (20 mM phosphate buffer with 2.7 mM KCl, 137 mM NaCl and 0.05% surfactant P20 (Tween™ 20)). The surface was regenerated with 10 mM glycine HCl at pH 1.7 for at least 180 sec and additional 60 sec. Human Aβ (1-40) peptide was used as a negative control.

Affinity measurements were performed using an optical biosensor T200 (Biacore®). Kinetic analysis was performed according to 1:1 binding fitting model with Biacore T200 Evaluation Software (version 2.0).

Figure 8:
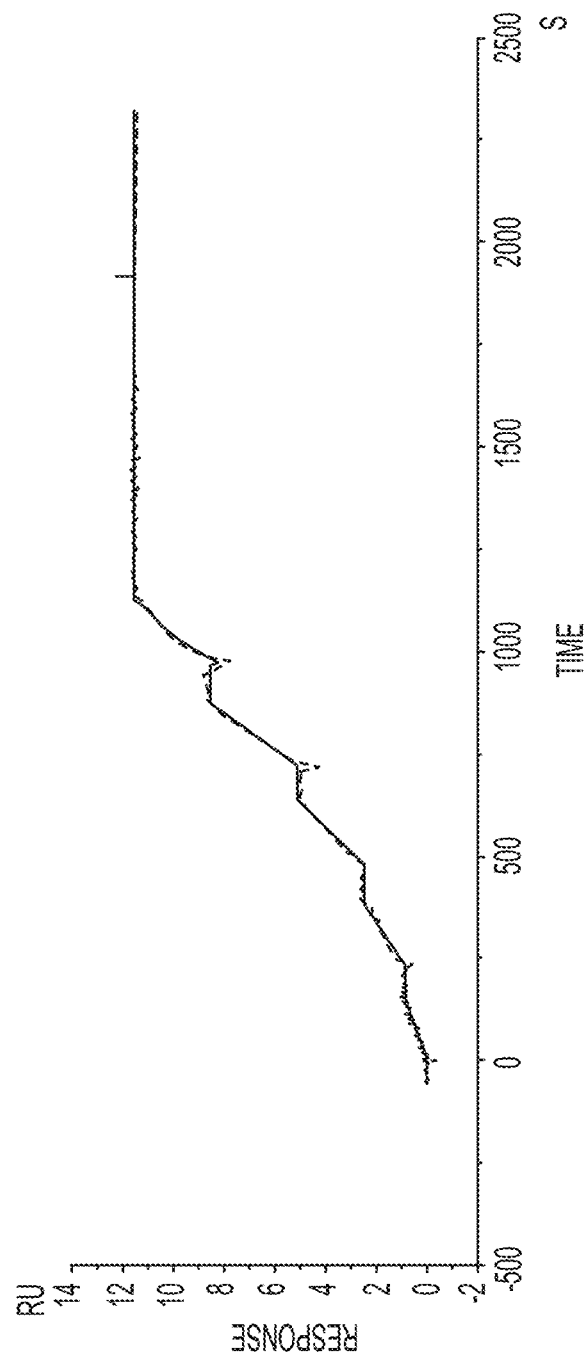
FIG. 8 is a sensorgram (single cycle kinetics) from surface plasmon resonance label-free detection of the affinity binding interaction of Aβ/pE3/1 to human Aβ(3pE-40) peptide.

Results: Kinetic analysis of monoclonal antibody Aβ/pE3/1 confirmed affinity binding to Aβ-3pE-40 peptide. Equilibrium binding constant (affinity, $K_D$) and kinetic rate constants ($k_a/k_d$) are shown in Table 3. Sensorgram (single cycle kinetics) demonstrating binding interactions of Aβ/pE3/1 to human Aβ-3pE-40 peptide is illustrated in FIG. 8.

TABLE 3

| Kinetics of Aβ/pE3/1 (n = 6) | | | | |
|---|---|---|---|---|
| Sample | | ka (1/Ms) | kd (1/s) | $K_D$ (M) |
| Aβ/pE3/1 | Mean | 1.12E+05 | 9.37E−05 | 8.53E−10 |
|  | CV | 1.32E−01 | 1.64E−01 | 2.35E−01 |

In describing the present invention and its various embodiments, specific terminology is employed for the sake of clarity. However, the invention is not intended to be limited to the specific terminology so selected. A person skilled in the relevant art will recognize that other equivalent components can be employed and other methods developed without departing from the broad concepts of the current invention. All references cited anywhere in this specification are incorporated by reference as if each had been individually incorporated.

We claim:

1. An isolated antibody or antigen binding fragment thereof which binds to amyloid β protein having pyroglutamate at the third amino acid residue (3pE Aβ) comprising
    a) a heavy chain variable region CDR1 comprising the amino acid sequence of SEQ ID NO:3,
    b) a heavy chain variable region CDR2 comprising the amino acid sequence of SEQ ID NO:4,
    c) a heavy chain variable region CDR3 comprising the amino acid sequence of SEQ ID NO:5,
    d) a light chain variable region CDR1 comprising the amino acid sequence of SEQ ID NO: 14,
    e) a light chain variable region CDR2 comprising the amino acid sequence of SEQ ID NO: 15, and
    f) a light chain variable region CDR3 comprising the amino acid sequence of SEQ ID NO:16.

2. The isolated antibody or antigen binding fragment thereof of claim 1 wherein the antibody is a monoclonal antibody.

3. A pharmaceutical composition comprising the antibody or antigen binding fragment thereof of claim 1 and a pharmaceutically acceptable carrier.

4. The isolated antibody or antigen binding fragment thereof of claim 1 wherein the antibody is a humanized antibody.

5. A pharmaceutical composition comprising the antibody or antigen binding fragment thereof of claim 4 and a pharmaceutically acceptable carrier.

6. The isolated antibody or antigen binding fragment thereof of claim 1 wherein
    a) the heavy chain variable region CDR1 is the amino acid sequence of SEQ ID NO:3,
    b) the heavy chain variable region CDR2 is the amino acid sequence of SEQ ID NO:4,
    c) the heavy chain variable region CDR3 is the amino acid sequence of SEQ ID NO:5,
    d) the light chain variable region CDR1 is the amino acid sequence of SEQ ID NO: 14,
    e) the light chain variable region CDR2 is the amino acid sequence of SEQ ID NO:15, and
    f) the light chain variable region CDR3 is the amino acid sequence of SEQ ID NO:16.

7. The isolated antibody or antigen binding fragment thereof of claim 6 wherein the antibody is a humanized antibody.

8. A pharmaceutical composition comprising the antibody or antigen binding fragment thereof of claim 7 and a pharmaceutically acceptable carrier.

9. A recombinant cell that produces the antibody of any one of claims 4 and 7.

10. The isolated antibody or antigen binding fragment thereof of claim 1 wherein
    a) the heavy chain variable region comprises the amino acid sequence of SEQ ID NO:2; and
    b) the light chain variable region comprising the amino acid sequence of SEQ ID NO:13.

11. The isolated antibody or antigen binding fragment thereof of claim 1 wherein the heavy chain variable region of the amino acid sequence that is at least 98% identical to the amino acid sequence of SEQ ID NO:2 comprises the heavy chain variable region CDR1 comprising the amino acid sequence of SEQ ID NO:3, the heavy chain variable region CDR2 comprising the amino acid sequence of SEQ ID NO:4, the heavy chain variable region CDR3 comprising the amino acid sequence of SEQ ID NO:5 and the light chain variable region of the amino acid sequence that is at least 98% identical to the amino acid sequence of SEQ ID NO: 13 comprises the light chain variable region CDR1 comprising the amino acid sequence of SEQ ID NO: 14, the light chain variable region CDR2 comprising the amino acid sequence of SEQ ID NO: 15, and the light chain variable region CDR3 comprising the amino acid sequence of SEQ ID NO:16.

12. The isolated antibody or antigen binding fragment thereof of claim 6 wherein the heavy chain variable region of the amino acid sequence that is at least 98% identical to the amino acid sequence of SEQ ID NO:2 comprises the heavy chain variable region CDR1 comprising the amino acid sequence of SEQ ID NO:3, the heavy chain variable region CDR2 comprising the amino acid sequence of SEQ ID NO:4, the heavy chain variable region CDR3 comprising the amino acid sequence of SEQ ID NO:5 and the light chain variable region of the amino acid sequence that is at least 98% identical to the amino acid sequence of SEQ ID NO: 13 comprises the light chain variable region CDR1 comprising the amino acid sequence of SEQ ID NO: 14, the light chain variable region CDR2 comprising the amino acid sequence of SEQ ID NO: 15, and the light chain variable region CDR3 comprising the amino acid sequence of SEQ ID NO:16.

13. The isolated antibody or antigen binding fragment thereof of any of claims 1, 6, 11 and 12 wherein the antibody competes for binding to 3pE Aβ with an antibody comprising a heavy chain of the amino acid sequence of SEQ ID NO: 1 and a light chain of the amino acid sequence of SEQ ID NO: 12.

14. An isolated antibody which binds to 3pE Aβ comprising
    a) a heavy chain of the amino acid sequence of SEQ ID NO: 1; and
    b) a light chain of the amino acid sequence of SEQ ID NO: 12.

15. A recombinant cell that produces the antibody of any one of claims 1, 6, 10, 2, or 14.

16. A method of producing monoclonal antibodies according to any one of claims 1, 6, 10, 2, or 14, comprising i) culturing the recombinant cell of claim 12, ii) harvesting a supernatant of the recombinant cell culture of the step i), iii) screening and detecting the antibody binding to 3pE Aβ peptides in the supernatant of the step ii) by immunoassays or ELISA, and iv) harvesting and isolating the antibody binding to 3pE Aβ according to any one of claims 1, 6, 10, 2, or 14 by 3pE Aβ peptide-affinity purification methods.

* * * * *